United States Patent
Ukita et al.

[11] Patent Number: 5,965,730
[45] Date of Patent: Oct. 12, 1999

[54] PYRIDINE DERIVATIVES

[75] Inventors: Tatsuzo Ukita, Kobe; Masakatsu Sugahara, Suita; Katsuo Ikezawa, Urawa; Hideo Kikkawa, Okegawa; Kazuaki Naito, Tokyo-to, all of Japan

[73] Assignee: Tanabe Seiyaku Co., Ltd., Osaka, Japan

[21] Appl. No.: 08/985,042

[22] Filed: Dec. 4, 1997

[30] Foreign Application Priority Data

Dec. 13, 1996 [JP] Japan .................................. 8-333357

[51] Int. Cl.⁶ ................... A61K 31/47; A61K 31/535; C07D 401/14; C07D 413/14

[52] U.S. Cl. ................... 544/128; 514/235.2; 514/253; 514/308; 544/235; 544/237; 544/284; 546/122; 546/140; 546/141; 546/144; 546/147; 546/167

[58] Field of Search .................... 544/128, 237; 546/144, 167; 514/253

[56] References Cited

U.S. PATENT DOCUMENTS 5,177,085  1/1993  Naef .
5,342,941  8/1994  Iwasaki et al. .

FOREIGN PATENT DOCUMENTS

0664289 A2  7/1995  European Pat. Off. .
748805A1   12/1996  European Pat. Off. .

*Primary Examiner*—Robert W. Ramsuer
*Attorney, Agent, or Firm*—Finnegan, Henderson, Farabow, Garrett & Dunner, L.L.P.

[57] ABSTRACT

A pyridine derivative of the formula (I):

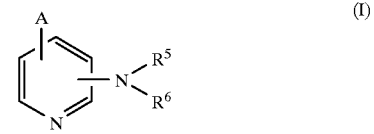

wherein A is group of the following formulae:

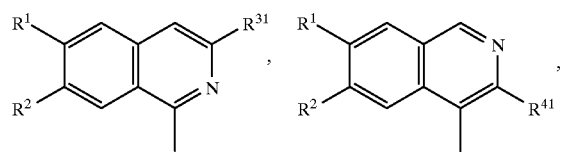

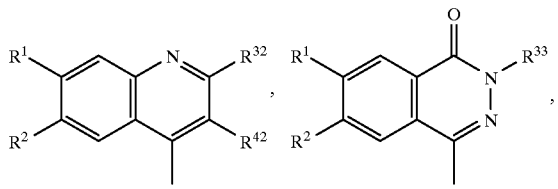

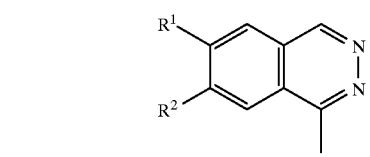

($R^1$ and $R^2$ are each H, or protected or unprotected OH, $R^{31}$, $R^{41}$ and $R^{42}$ are protected or unprotected hydroxymethyl, $R^{32}$ is H, lower alkyl, or protected or unprotected hydroxymethyl, $R^{33}$ is substituted or unsubstituted lower alkyl, and the dotted line means the presence or absence of a double bond), $R^5$ and $R^6$ are H, or protected or unprotected amino, or both combine together with the adjacent nitrogen to form substituted or unsubstituted heterocycle, or a pharmaceutically acceptable salt thereof, these compounds showing excellent bronchoconstriction inhibitory activity and/or anti-inflammatory activity of airway, and being useful in the prophylaxis or treatment of asthma.

17 Claims, No Drawings

PYRIDINE DERIVATIVES

TECHNICAL FIELD

The present invention relates to a novel pyridine derivative exhibiting a selective phosphodiesterase IV inhibitory activity, and a potent inhibitory activity of bronchoconstriction and/or an anti-inflammatory activity of airway, a process for preparing the same, and an intermediate therefor.

PRIOR ART

European Patent Publication EP-557016-A1 (=U.S. Pat. No. 5,342,941) discloses that some compounds such as 1-(3-pyridyl)-2,3-bis(hydroxymethyl)-6,7-diethoxynaphthalene exhibit an anti-asthmatic activity. European Patent Publication EP-664289-A2 and European Patent Publication EP-490823-A1 (=U.S. Pat. No. 5,177,085) disclose that some compounds such as 3,4-dihydro-6,7-dimethoxy-1-(3,5-dimethoxyphenyl)-3-hydroxymethyl-isoquinoline exhibit an anti-asthmatic activity. However, they never disclose compounds wherein the pyridine ring is substituted by a nitrogen-containing heterocyclic fused ring and an unsubstituted or substituted amino group such as the compounds of the present invention.

On the other hand, it is known that cAMP and cGMP, which are intracellular second messengers, are decomposed and inactivated by phosphodiesterase (abbreviated as "PDE"). Currently, at least seven different PDE isozyme gene families are recognized and these PDEs widely distributes in many cell types and tissues of the living body. A PDE inhibitor inhibits said PDE, by which the level of cAMP and cGMP in tissue cells is increased, and as a result, a PDE inhibitor exhibits various pharmacological activities, for example, relaxation of vascular smooth muscle and bronchial smooth muscle, and induction of positive inotropic action and chronotropic action in the heart. Moreover, a PDE inhibitor can control the central function owing to increase of cAMP in the central system, i.e., it can exhibit an anti-depressant activity, and improve memory learning functions. In addition, a PDE inhibitor shows inhibition of platelet aggregation and inhibition of activation of inflammatory cells, and further shows lipocatabolic action of fatty cells [cf. Trends in Pharmacological Sciences, 12, 19–27, 1991].

Therefore, an agent inhibiting PDE is considered to be useful in the treatment of various diseases, such as bronchial asthma, thrombosis, depression, central hypofunction after cerebrovascular obstruction, cerebrovascular dementia, Alzheimer's type dementia, various inflammations, obesity, and heart failure.

On the other hand, various anti-asthmatic agents have been known, but those known agents have some defects such as insufficiency in effects of inhibiting bronchoconstriction and further insufficient removal of side effects on the heart, and hence, it has been demanded to develop a new type drug.

Hitherto, theophylline has been used in the treatment of asthma as a PDE inhibitor. However, since the PDE inhibitory activity of this drug is nonspecific, it shows cardiotonic and central activities in addition to relaxation activity of bronchial smooth muscle. Therefore, careful attention has to be paid to this agent in view of such side effects. Accordingly, under the circumstances, it has been desired to develop a new medicament which can selectively inhibit phosphodiesterase IV (PDE IV) which largely exists much more in the bronchial smooth muscle and the inflammatory cells unlike other isozymes of PDE.

BRIEF DESCRIPTION OF INVENTION

An object of the present invention is to provide a novel pyridine derivative showing a selective PDE IV inhibitory activity, and a potent inhibitory activity of bronchoconstriction and/or an anti-inflammatory activity of airway, and being useful in the prophylaxis or treatment of asthma. Another object of the present invention is to provide a process for preparing a novel pyridine derivative. Still further object of the present invention is to provide an intermediate for preparing the same.

DETAILED DESCRIPTION OF INVENTION

The present invention relates to a pyridine derivative of the formula (I):

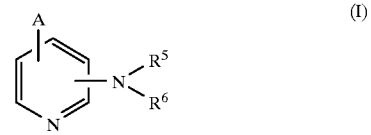

wherein A is a group selected from the following formulae:

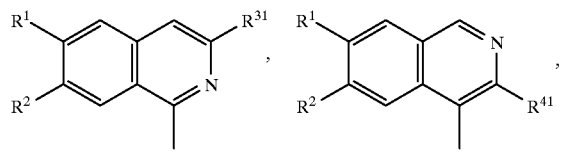

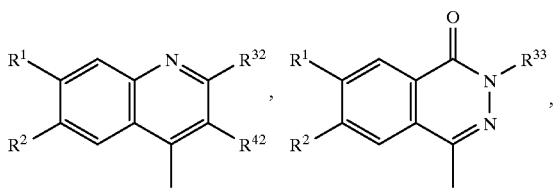

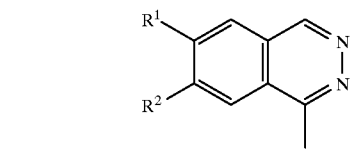

(in which $R^1$ and $R^2$ are the same or different and each a hydrogen atom, or a protected or unprotected hydroxy group, $R^{31}$ is a protected or unprotected hydroxymethyl group, $R^{32}$ is a hydrogen atom, a lower alkyl group, or a protected or unprotected hydroxymethyl group, $R^{33}$ is a substituted or unsubstituted lower alkyl group, $R^{41}$ is a protected or unprotected hydroxymethyl group, $R^{42}$ is a protected or unprotected hydroxymethyl group, and the dotted line means the presence or absence of a double bond).

$R^5$ and $R^6$ are the same or different and each a hydrogen atom, or a protected or unprotected amino group, or both may combine at their termini together with the adjacent nitrogen atom to which they bond to form a substituted or unsubstituted heterocyclic group, or a pharmaceutically acceptable salt thereof.

The desired compound (I) of the present invention or a pharmaceutically acceptable salt thereof shows a selective PDE IV inhibitory activity, and a potent inhibitory activity of bronchoconstriction and/or an anti-inflammatory activity of airway, so that the present compound (I) is a useful medicament in the prophylaxis or treatment of asthma. For example, the present compound (I) shows a more potent inhibitory activity on the antigen-induced bronchoconstriction than theophylline does, and is characteristic in the potent inhibitory effect on the bronchoconstriction but no side effects on the heart.

When $R^1$ and/or $R^2$ of the present compound (I) are a protected hydroxy group, the protecting group for hydroxy group may be any pharmaceutically acceptable protecting groups for hydroxy group, for example, a substituted or unsubstituted lower alkanoyl group, a substituted or unsubstituted alkyl group, or a substituted or unsubstituted cycloalkyl group. Preferable protecting group is an alkyl group, more preferably a lower alkyl group.

When $R^{31}$, $R^{32}$, $R^{33}$, $R^{41}$ and/or $R^{42}$ are a protected hydroxymethyl group, the protecting group for hydroxy of the hydroxymethyl group may be any pharmaceutically acceptable protecting group for hydroxy group, for example, ones which are easily hydrolyzed in the living body but does not produce any harmful side-products, such as a substituted or unsubstituted lower alkanoyl group, a substituted or unsubstituted alkyl group, a substituted or unsubstituted lower alkoxycarbonyl group, or a substituted or unsubstituted cycloalkyl group.

The "substituted or unsubstituted lower alkanoyl group" includes a lower alkanoyl group which may optionally be substituted by one or two groups selected from a protected or unprotected amino group, a carboxyl group, a lower alkoxycarbonyl group, a hydroxy group and a lower alkoxy group. The "substituted or unsubstituted alkyl group" includes an alkyl group which may optionally be substituted by a group selected from a lower alkoxycarbonyl group, a lower alkoxy group, an aryl group, and a lower alkyl-substituted piperazinylcarbonyl group. The aryl group includes, for example, a phenyl group, a lower alkoxyphenyl group, and a naphthyl group.

The protecting group of the protected amino group which is one of the substituents of the "substituted or unsubstituted lower alkanoyl group" may be any protecting groups for amino group, for example, an acyl group such as a lower alkanoyl group (e.g., acetyl, propionyl), a lower alkoxycarbonyl group, or a phenyl-lower alkoxycarbonyl group (e.g., benzyloxycarbonyl).

The "substituted lower alkyl group" for $R^{33}$ includes a lower alkyl group which is substituted by a group selected from a pyridyl group, a cyclo-lower alkyl group and a hydroxy group.

The heterocyclic group formed by combining $R^5$ and $R^6$ at their termini together with the adjacent nitrogen atom to which they bond includes a heteromonocyclic, heterobicyclic or heterotricyclic group having optionally a heteroatom selected from a nitrogen atom, an oxygen atom and a sulfur atom in addition to said adjacent nitrogen atom.

Suitable examples of such heterocyclic group are pyridyl, quinolyl, isoquinolyl, cyclopenta[b]pyridyl, pyrro[2,3-b]pyridyl, imidazo[4,5-b]pyridyl, pyrido[2,3-d]thiazolyl, pyrido[2,3-d]oxazolyl, naphthyridinyl, quinoxazolinyl, phthalazinyl, quinazolinyl, indolyl, pyridazinyl, thieno[2,3-d]pyridazinyl, azepinyl, azetidyl, isoindolyl, pyrrolyl, benzazepinyl, phenanthridinyl, benzothiadinyl, benzimidazolinyl, pyrazinyl or morpholino (these heterocyclic groups optionally being hydrogenated partially or wholly). Among these groups, preferable ones are pyridyl, quinolyl, isoquinolyl, naphthyridinyl, phthalazinyl, quinozolinyl or thieno[2,3-d]pyridazinyl (these heterocyclic groups optionally being hydrogenated partially or wholly).

When one or both $R^5$ and $R^6$ are a protected amino group, the protecting group for amino group may be any pharmaceutically acceptable protecting groups for amino group, for example, a lower alkanoyl group or a phenyl-lower alkoxycarbonyl group.

On the other hand, the above-mentioned heterocyclic groups may optionally be substituted by one or more groups which are the same or different, and selected from (1) a lower alkenyl group; (2) a lower alkynyl group; (3) a lower alkylthio group; (4) a cycloalkyl group; (5) a trifluoromethyl group; (6) a cyano group; (7) a tetrazolyl group; (8) a formyl group; (9) an amino group; (10) a mono- or di-lower alkylamino group wherein the lower alkyl moiety may optionally be substituted by a group selected from a morpholino group, a monocycloalkyl-substituted amino group, a pyridyl group, an imidazolyl group, a piperidyl group or a pyrrolidinyl group; (11) a pyridyl group; (12) a morpholino group; (13) a lower alkyl-substituted triazolyl group; (14) a bis-(hydroxy-lower alkyl)aminocarbonyl group; (15) a bis (tri-lower alkylsilyloxy-lower alkyl)aminocarbonyl group; (16) a morpholinocarbonyl group; (17) a lower alkyl-substituted piperazinylcarbonyl group; (18) a hydroxy-lower alkyl-substituted piperazinylcarbonyl group; (19) a tri-lower alkylsilyloxy-lower alkyl-substituted piperazinylcarbonyl group; (20) a lower alkoxycarbonyl group; (21) a carboxyl group; (22) a lower alkyl group which may optionally be substituted by a morpholino group or a pyridyl group; (23) a lower alkoxy group which may optionally be substituted by a group selected from a piperidyl group, a pyridyl group, a hydroxy group, or a lower alkoxy group; (24) an oxo group; (25) a hydroxy group; (26) a pyrimidinyl group; (27) a phenyl group which may optionally be substituted by a di-lower alkylamino group or a halogen atom; (28) a halogen atom; (29) a nitro group; (30) an imidazolyl group; (31) a lower alkylenedioxy group; (32) a thiazolyl group; and (33) a thienyl group.

Among these groups, more preferable substituents are one or more groups which are the same or different and selected from (1) an amino group; (2) a pyridyl group; (3) a lower alkyl group which may optionally be substituted by a morpholino group or a pyridyl group; (4) a lower alkoxy group which may optionally be substituted by a pyridyl group; (5) an oxo group; (6) a pyrimidinyl group; (7) a phenyl group which may optionally be substituted by a di-lower alkylamino group or a halogen atom; (8) a halogen atom; (9) a thiazolyl group; and (10) a thienyl group.

Among the substituted heterocyclic groups, pharmaceutically preferable heterocyclic groups are ones which are substituted at least by an oxo group, a hydroxy group or an amino group, especially ones substituted at least by an oxo group. The heterocyclic groups substituted at least by an oxo group are heterocyclic groups having a partial structure of the formula:

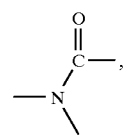

and the suitable examples of such heterocyclic groups are exemplified as follow.

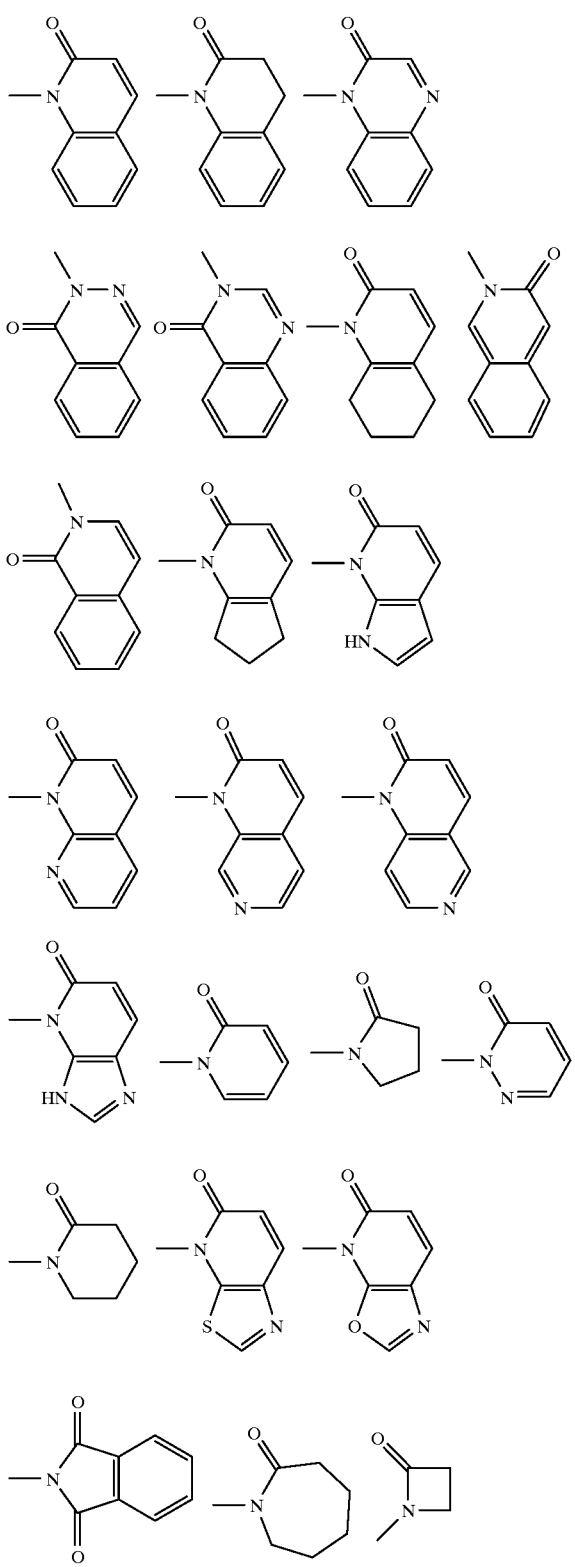

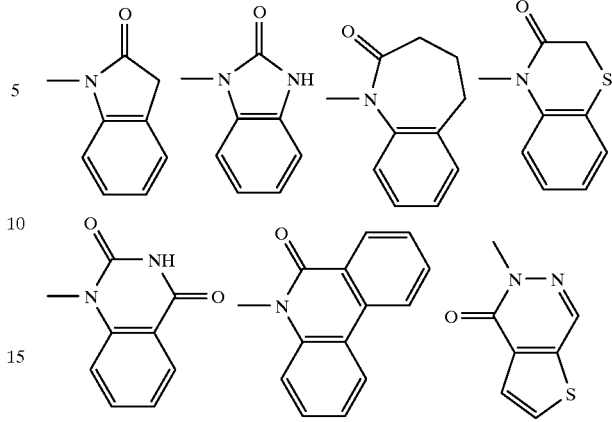

(these heterocyclic groups substituted by an oxo group may optionally be further substituted by one or two groups selected from (1) a lower alkenyl group; (2) a lower alkynyl group; (3) a lower alkylthio group; (4) a cycloalkyl group; (5) a trifluoromethyl group; (6) a cyano group; (7) a tetrazolyl group; (8) a formyl group; (9) an amino group; (10) a mono- or di-lower alkylamino group wherein the lower alkyl moiety may be substituted optionally by a group selected from a morpholino group, a monocycloalkyl-substituted amino group, a pyridyl group, an imidazolyl group, a piperidyl group and a pyrrolidinyl group; (11) a pyridyl group; (12) a morpholino group; (13) a lower alkyl-substituted triazolyl group; (14) a bis(hydroxy-lower alkyl) aminocarbonyl group; (15) a bis(tri-lower alkylsilyloxy-lower alkyl)aminocarbonyl group; (16) a morpholinocarbonyl group; (17) a lower alkyl-substituted piperazinylcarbonyl group; (18) a hydroxy-lower alkyl-substituted piperazinylcarbonyl group; (19) a tri-lower alkylsilyloxy-lower alkyl-substituted piperazinylcarbonyl group; (20) a lower alkoxycarbonyl group; (21) a carboxyl group; (22) a lower alkyl group which may optionally be substituted by a morpholino group or a pyridyl group; (23) a lower alkoxy group which may optionally be substituted by a group selected from a piperidyl group, a pyridyl group, a hydroxy group, and a lower alkoxy group; (24) an oxo group; (25) a hydroxy group; (26) a pyrimidinyl group; (27) a phenyl group which may optionally be substituted by a di-lower alkylamino group or a halogen atom; (28) a halogen atom; (29) a nitro group; (30) an imidazolyl group; (31) a lower alkylenedioxy group; (32) a thiazolyl group; and (33) a thienyl group).

When $R^5$ and $R^6$ of the formula (I) combine at their termini together with the adjacent nitrogen atom to form a substituted or unsubstituted heterocyclic group, the suitable examples of the substituted or unsubstituted heterocyclic group are (1) an oxo-substituted dihydroquinolyl group which may optionally be substituted by a pyridyl group, (2) an oxo-substituted dihydroisoquinolyl group which may optionally be substituted by a morpholino-substituted lower alkoxy group or a pyridyl-substituted lower alkoxy group, (3) an oxo-substituted dihydrophthalazinyl group which may optionally be substituted by a group selected from a lower alkyl group being optionally substituted by a pyridyl group; a pyrimidinyl group; a lower alkoxy group; a halogen atom; a pyridyl group; a thiazolyl group; a phenyl group being optionally substituted by a di-lower alkylamino group or a halogen atom; and a thienyl group, (4) an oxo-substituted dihydropyridyl group which may optionally be substituted by a pyridyl group, (5) an oxo-substituted dihydronaphthyridinyl group, (6) a di-oxo-substituted dihydroquinazolinyl group which may optionally be substituted by a lower alkyl group, and (7) an oxo-substituted thienopyridazinyl group which may optionally be substituted by a tri-lower alkoxy-substituted phenyl group.

Among the present compounds (I), preferable compounds are compounds of the formula (I) wherein A is a group selected from the following formulae:

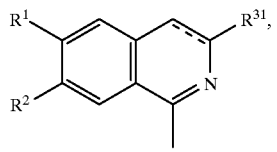

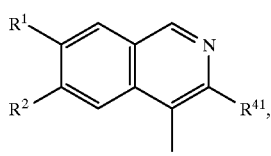

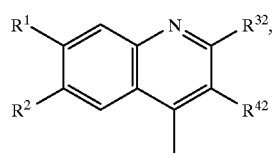

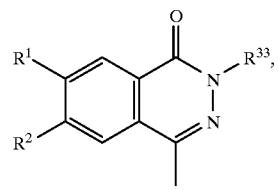

(in which $R^1$ and $R^2$ are the same or different and each a lower alkoxy group, $R^{31}$ is a hydroxymethyl group which may optionally be substituted by a lower alkylcarbonyl group, $R^{32}$ is a hydrogen atom or a hydroxymethyl group, $R^{33}$ is a methyl group being substituted by a cyclo-lower alkyl group or a hydroxy group, $R^{41}$ is a hydroxymethyl group, $R^{42}$ is a hydroxymethyl group, and the dotted line means the presence or absence of a double bond), and the substituted or unsubstituted heterocyclic group formed by combining $R^5$ and $R^6$ at their termini together with the adjacent nitrogen atom to which they bond is a group selected from (1) an oxo-substituted dihydroisoquinolyl group which is substituted by a group selected from a morpholino-substituted lower alkoxy group and a pyridyl-substituted lower alkoxy group, (2) an oxo-substituted dihydrophthalazinyl group which may optionally be substituted by a group selected from a lower alkyl group being optionally substituted by a pyridyl group; a pyrimidinyl group; a lower alkoxy group; a halogen atom; a pyridyl group; a thiazolyl group; a phenyl group being optionally substituted by a di-lower alkylamino group or a halogen atom; and a thienyl group, (3) an oxo-substituted dihydronaphthyridinyl group, (4) a di-oxo-substituted dihydroquinazolinyl group, and (5) an oxo-substituted thienopyridazinyl group which is substituted by a tri-lower alkoxy-substituted phenyl group.

Among the present compounds (I), pharmaceutically preferable compounds are compounds of the formula (I) wherein A is a group selected from the following formulae:

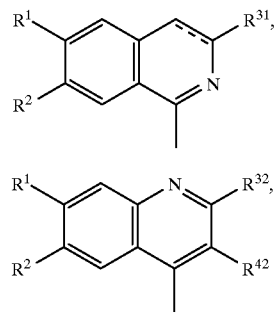

(in which $R^1$ and $R^2$ are the same or different and each a lower alkoxy group, $R^{31}$ is a hydroxymethyl group which may optionally be substituted by a lower alkylcarbonyl group, $R^{32}$ is a hydrogen atom or a hydroxymethyl group, $R^{42}$ is a hydroxymethyl group, and the dotted line means the presence or absence of a double bond), and the substituted or unsubstituted heterocyclic group formed by combining $R^5$ and $R^6$ at their termini together with the adjacent nitrogen atom to which they bond is a group selected from (1) an oxo-substituted dihydroisoquinolyl group which is substituted by a group selected from a morpholino-substituted lower alkoxy group and a pyridyl-substituted lower alkoxy group, and (2) an oxo-substituted dihydrophthalazinyl group which may optionally be substituted by a group selected from a lower alkyl group, a pyrimidinyl group, a lower alkoxy group, a pyridyl group, a thiazolyl group, a phenyl group, and a thienyl group.

Among the present compounds (I), pharmaceutically more preferable compounds are compounds of the formula (I) wherein A is a group of the formula:

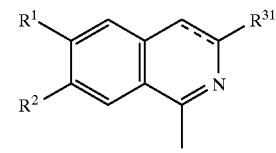

(in which $R^1$ and $R^2$ are the same or different and each a lower alkoxy group, $R^{31}$ is a hydroxymethyl group which may optionally be substituted by a lower alkylcarbonyl group, and the dotted line means the presence or absence of an double bond), and the substituted or unsubstituted heterocyclic group formed by combining $R^5$ and $R^6$ at their termini together with the adjacent nitrogen atom to which they bond is a group selected from (1) an oxo-substituted dihydroisoquinolyl group which is substituted by a morpholino-substituted lower alkoxy group, and (2) an oxo-substituted dihydrophthalazinyl group which may optionally be substituted by a group selected from a lower alkyl group, a pyridyl group, and a thiazolyl group.

Among these compounds, pharmaceutically preferable other compounds are compounds of the formula (I) wherein A is a group of the formula:

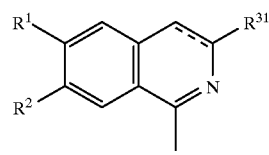

(in which $R^1$ and $R^2$ are the same or different and each a lower alkoxy group, $R^{31}$ is a hydroxymethyl group which may optionally be substituted by a lower alkylcarbonyl group, and the dotted line means the presence or absence of an double bond), and the substituted or unsubstituted heterocyclic group formed by combining $R^5$ and $R^6$ at their termini together with the adjacent nitrogen atom to which they bond is a group selected from (1) an oxo-substituted dihydroisoquinolyl group which is substituted by a group selected from a morpholino-substituted lower alkoxy group and a pyridyl-substituted lower alkoxy group, (2) an oxo-substituted dihydrophthalazinyl group which is substituted by a group selected from a lower alkyl group; a lower alkoxy group; a halogen atom; a pyridyl group; a thiazolyl group; a phenyl group being optionally substituted by a di-lower alkylamino group or a halogen atom; and a thienyl group, and (3) an oxo-substituted thienopyridazinyl group which is substituted by a tri-lower alkoxy-substituted phenyl group.

Among these compounds, pharmaceutically more preferable other compounds are compounds of the formula (I) wherein A is a group of the formula:

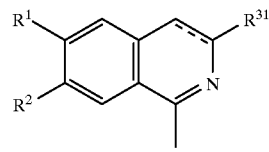

(in which $R^1$ and $R^2$ are the same or different and each a lower alkoxy group, $R^{31}$ is a hydroxymethyl group, and the dotted line means the presence or absence of an double bond), and the substituted or unsubstituted heterocyclic group formed by combining $R^5$ and $R^6$ at their termini together with the adjacent nitrogen atom to which they bond is a group selected from (1) an oxo-substituted dihydroisoquinolyl group which is substituted by a group selected from a morpholino-substituted lower alkoxy group and a pyridyl-substituted lower alkoxy group, (2) an oxo-substituted dihydrophthalazinyl group which is substituted by a group selected from a lower alkoxy group; a halogen atom; a pyridyl group; a thiazolyl group; a phenyl group being optionally substituted by a di-lower alkylamino group or a halogen atom; and a thienyl group, and (3) an oxo-substituted thienopyridazinyl group which is substituted by a tri-lower alkoxy-substituted phenyl group.

Among these compounds, pharmaceutically most preferable compounds are compounds of the formula (1) wherein A is a group of the formula:

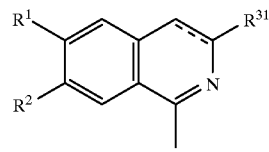

(in which $R^1$ and $R^2$ are the same or different and each a lower alkoxy group, $R^{31}$ is a hydroxymethyl group, and the dotted line means the presence or absence of a double bond), and the substituted or unsubstituted heterocyclic group formed by combining $R^5$ and $R^6$ at their termini together with the adjacent nitrogen atom to which they bond is a group selected from (1) an oxo-substituted dihydroisoquinolyl group which is substituted by a morpholino-substituted lower alkoxy group; and (2) an oxo-substituted dihydrophthalazinyl group which is substituted by a group selected from a pyridyl group and a thiazolyl group.

Pharmaceutically preferable other compounds are compounds of the formula (I) wherein A is a group of the formula:

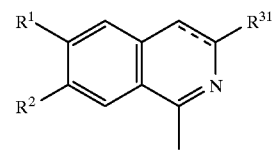

(in which wherein $R^1$ and $R^2$ are the same or different and each a lower alkoxy group, $R^{31}$ is a hydroxymethyl group, and the dotted line means the presence or absence of a double bond), and the substituted or unsubstituted heterocyclic group formed by combining $R^5$ and $R^6$ at their termini together with the adjacent nitrogen atom to which they bond is an oxo-substituted dihydrophthalazinyl group which may optionally be substituted by a group selected from a lower alkyl group being optionally substituted by a pyridyl group; a pyrimidinyl group; a lower alkoxy group; a halogen atom; a pyridyl group; a thiazolyl group; a phenyl group being optionally substituted by a di-lower alkylamino group or a halogen atom; and a thienyl group.

Pharmaceutically preferable other compounds are compounds of the formula (I) wherein the heterocyclic group formed by combining $R^5$ and $R^6$ at their termini together with the adjacent nitrogen atom to which they bond is a group of the formula:

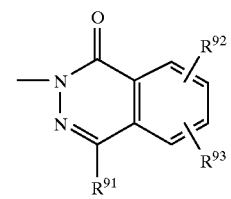

wherein $R^{91}$, $R^{92}$ and $R^{93}$ are the same or different and each a hydrogen atom; a thienyl group; a halogen atom; a lower alkoxy group; a lower alkyl group which may optionally be substituted by a pyridyl group; a phenyl group which may optionally be substituted by a di-lower alkylamino group, a lower alkoxy group or a halogen atom; a pyridyl group; a pyrimidinyl group; or a thiazolyl group. Among these compounds, more preferable compounds are compounds of the formula (I) wherein $R^{91}$, $R^{92}$ and $R^{93}$ are the same or different and each a hydrogen atom; a thienyl group; a halogen atom; a lower alkoxy group; a phenyl group which may optionally be substituted by a di-lower alkylamino group or a halogen atom; a pyridyl group; or a thiazolyl group.

In the formula (I), the preferable substitution position of A is 4-position of the pyridine ring, and the preferable substitution position of —$NR^5R^6$ is 2-position of the pyridine ring.

Among these pharmaceutically preferable compounds (I), the compound of the formula (I) wherein $R^1$ and $R^2$ are the same or different and each a lower alkoxy group, $R^{31}$ is a hydroxymethyl group, $R^{32}$ is a hydroxymethyl group, $R^{33}$ is a hydroxymethyl group, $R^{41}$ is a hydroxymethyl group and $R^{42}$ is a hydroxymethyl group is more preferable.

The compound (I) of the present invention may exist in the form of an optically active isomer thereof owing to asymmetric carbon atoms thereof, and the present invention also includes these optical isomers and a mixture thereof.

The present compounds (I) can clinically be used either in the free form or in the form of a pharmaceutically acceptable salt thereof. The pharmaceutically acceptable salt includes a salt with an inorganic acid such as hydrochloride, sulfate or hydrobromide, or a salt with an organic acid such as acetate, fumarate, oxalate, methanesulfonate or maleate. The compounds (I) having a substituent such as a carboxyl group may clinically be used in the form of a basic salt such as an alkali metal salt (e.g., sodium salt, potassium salt) or an alkaline earth metal salt (e.g., calcium salt) as well.

The desired compound (I) or a salt thereof includes either intracellular salt or an additive thereof, and solvates or hydrates thereof.

The present compound (I) or a pharmaceutically acceptable salt thereof can be administered either orally or parenterally, and can be formulated into a conventional pharmaceutical preparation such as tablets, granules, capsules, powders, injections, and inhalants.

The dose of the compounds (I) of the present invention or a pharmaceutically acceptable salt thereof may vary in accordance with, for example, the administration routes, and the ages, weights and conditions of the patients, but it is usually in the range of about 0.001–10 mg/kg/day, preferably in the range of about 0.003–3 mg/kg/day.

The compounds (I) of the present invention may be prepared by the following Processes A, B, and C.

Process A

Among the desired compounds (I), the compounds of the formula (I-a):

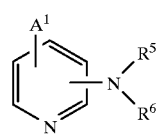

(I-a)

wherein $A^1$ is a group selected from the following formulae:

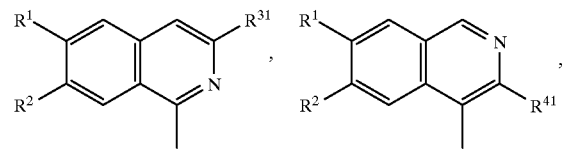

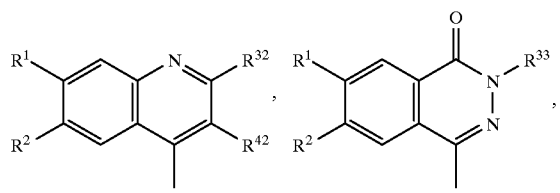

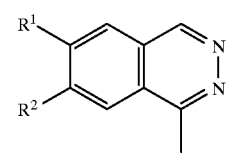

(in which $R^1$ and $R^2$ are the same or different and each a hydrogen atom, or a protected or unprotected hydroxy group, $R^{31}$ is a protected or unprotected hydroxymethyl group, $R^{32}$ is a hydrogen atom, a lower alkyl group, or a protected or unprotected hydroxymethyl group, $R^{33}$ is a substituted or unsubstituted lower alkyl group, $R^{41}$ is a protected or unprotected hydroxymethyl group, and $R^{42}$ is a protected or unprotected hydroxymethyl group), $R^5$ and $R^6$ are the same or different and each a hydrogen atom, or a protected or unprotected amino group, or both may combine at their termini together with the adjacent nitrogen atom to which they bond to form a substituted or unsubstituted heterocyclic group, may be prepared by reacting a compound of the formula (II):

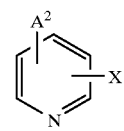

(II)

wherein $A^2$ is a group selected from the following formulae:

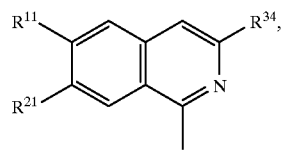

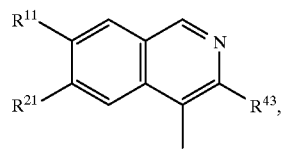

-continued

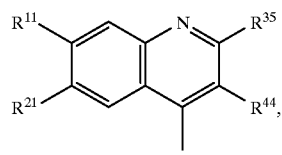

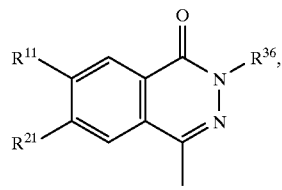

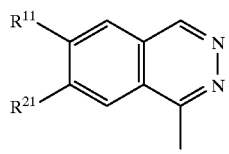

(in which $R^{11}$ and $R^{21}$ are the same or different and each a hydrogen atom, or a protected or unprotected hydroxy group, $R^{34}$ is a protected or unprotected hydroxymethyl group, $R^{35}$ is a hydrogen atom, a lower alkyl group, or a protected or unprotected hydroxymethyl group, $R^{36}$ is a substituted or unsubstituted lower alkyl group, $R^{43}$ is a protected or unprotected hydroxymethyl group, and $R^{44}$ is a protected or unprotected hydroxymethyl group), and X is a halogen atom, with a nitrogen-containing compound of the formula (III):

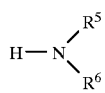

wherein $R^5$ and $R^6$ are the same as defined above, and when the product has a hydroxy group and/or a hydroxymethyl group, then if necessary introducing a protecting group onto the hydroxy moiety of the product, or when the product has a protected hydroxy group and/or a protected hydroxymethyl group, then if necessary removing the protecting groups from the product, and further if necessary, followed by converting the product into a pharmaceutically acceptable salt thereof.

Process B

Among the desired compounds (I), the compound of the formula (I-b):

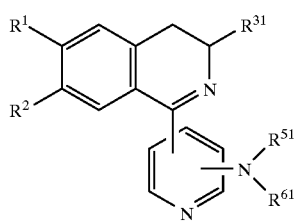

wherein $R^{51}$ and $R^{61}$ combine at their termini together with the adjacent nitrogen atom to which they bond to form a heterocyclic group which is substituted at least by an oxo group, and the other symbols are the same as defined above, may be prepared by subjecting a compound of the formula (IV):

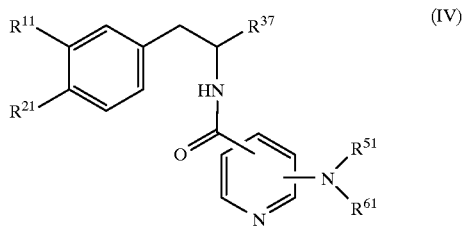

wherein $R^{37}$ is a protected hydroxymethyl group, and the other symbols are the same as defined above, or a salt thereof, to intramolecular cyclization reaction, and when the product has a hydroxy group, then if necessary introducing a protecting group onto the hydroxy group of the product, or when the product has a protected hydroxy group and/or a protected hydroxymethyl group, then if necessary removing protecting groups from the product, and further if necessary, followed by converting the product into a pharmaceutically acceptable salt thereof.

Process C

Among the desired compounds (I), the compound of the formula (I-c):

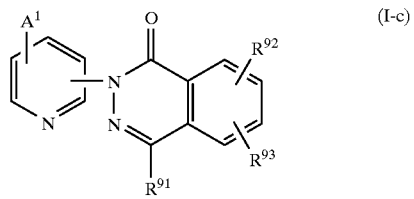

wherein $R^{91}$, $R^{92}$ and $R^{93}$ are the same or different and each a hydrogen atom; a thienyl group; a halogen atom; a lower alkoxy group; a lower alkyl group which may optionally be substituted by a pyridyl group; a phenyl group which may optionally be substituted by a di-lower alkylamino group, a lower alkoxy group, or a halogen atom; a pyridyl group; a pyrimidinyl group; or a thiazolyl group, and the other symbols are the same as defined above, or the compound of the formula (I-d):

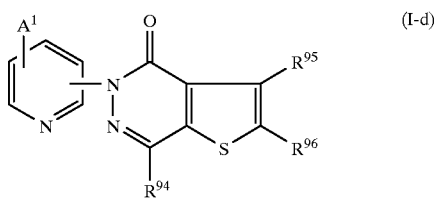

wherein $R^{94}$, $R^{95}$ and $R^{96}$ are the same or different and each a hydrogen atom; a thienyl group; a halogen atom; a lower alkoxy group; a lower alkyl group which may optionally be substituted by a pyridyl group; a phenyl group which may optionally be substituted by a di-lower alkylamino group, a lower alkoxy group or a halogen atom; a pyridyl group; a pyrimidinyl group; or a thiazolyl group, and $A^1$ are the same as defined above, may be prepared by reacting a compound of the formula (I-e):

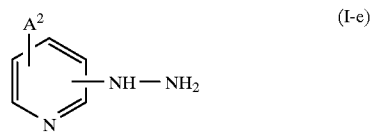

wherein $A^2$ is the same as defined above, or a salt thereof, with a carboxylic acid derivative of the formula (V):

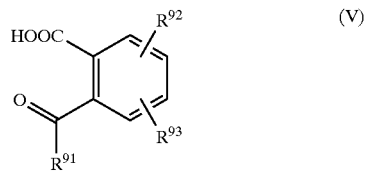

wherein the symbols are the same as defined above, or a salt thereof, or a carboxylic acid derivative of the formula (VI):

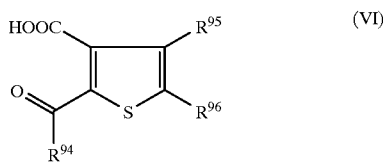

wherein the symbols are the same as defined above, or a salt thereof, and when the product has a hydroxy group and/or a hydroxymethyl group, then if necessary introducing a protecting group onto the hydroxy moiety of the product, or when the product has a protected hydroxy group and/or a protected hydroxymethyl group, then if necessary removing protecting groups from the product, and further if necessary, followed by converting the product into a pharmaceutically acceptable salt thereof.

The above Processes A, B and C are carried out as follows.

Process A

The reaction of the compound (II) and the nitrogen-containing compound (III) is carried out in the presence of a base and a copper catalyst in a suitable solvent. The base includes, for example, an alkali metal hydride, an alkali metal carbonate, and the copper catalyst includes, for example, copper (I) iodide, copper (I) bromide, copper (0) powder, copper (I) oxide, and copper (II) bromide, etc. The solvent includes, for example, dimethylformamide, dimethylsulfoxide, dimethylacetamide, toluene, and xylene. The reaction is preferably carried out at a temperature of from 80° C. to 160° C., preferably at a temperature of from 120° C. to 150° C.

Process B

The intramolecular cyclization reaction of the compound (IV) is carried out in the presence or absence of an acid catalyst in a suitable solvent. The acid catalyst includes, for example, phosphorus oxychloride, phosphorus pentachloride, aluminum chloride, thionyl chloride, chloroacetic anhydride, zinc chloride, alumina, phosphorus oxybromide, silica chloride, and polyphosphoric acid, and the solvent includes, for example, acetonitrile, toluene, xylene, and chloroform. The reaction is preferably carried out at a temperature of from 50° C. to 180° C., preferably at a temperature of from 80° C. to 120° C.

Process C

The reaction is carried out in a suitable solvent (e.g., a lower alkanol, ethylene glycol, dioxane, and toluene) at a temperature of from 100° C. to 140° C.

In the above Processes A, B and C, when $R^{11}$ and/or $R^{21}$ are a protected hydroxy group, and $R^{34}$, $R^{35}$, $R^{36}$, $R^{43}$ and/or $R^{44}$ are a protected hydroxymethyl group, the removal of these protecting groups from the product is carried out by a conventional method such as hydrolysis, acid-treatment, reduction, etc., which should be selected according to the types of the protecting groups to be removed. Moreover, the protection of the 6- and/or 7-hydroxy moieties, and the 2- and/or 3-hydroxymethyl moieties is carried out by a conventional method, i.e. by condensing each product with an acid anhydride or an acid halide of a lower alkanoic acid or a cycloalkanoic acid which correspond to the protecting groups for $R^1$, $R^2$, $R^{31}$, $R^{32}$, $R^{33}$, $R^{41}$ and/or $R^{41}$, or a lower alkyl halide which may optionally be substituted by a lower alkoxycarbonyl group, or a protected or unprotected carboxyl-substituted lower alkyl sulfonate. The reaction is preferably carried out in the presence of a base (e.g., triethylamine, pyridine, dimethylaminopyridine, sodium hydride, hexamethylphosphoric triamide) in a suitable solvent (e.g., methylene chloride, tetrahydrofuran) or without a solvent.

The starting compound (II) of the present invention is a novel compound, and can be prepared by the following processes.

Among the compounds (II), the isoquinoline compound of the formula (II-a) can be prepared as follows.

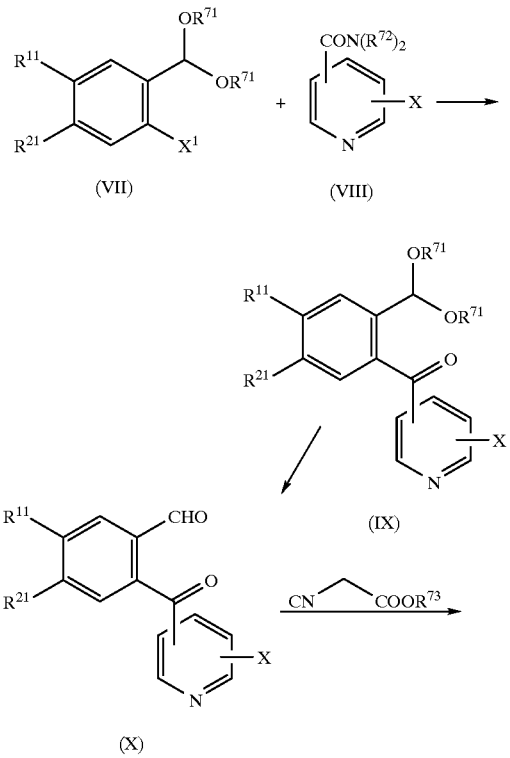

-continued

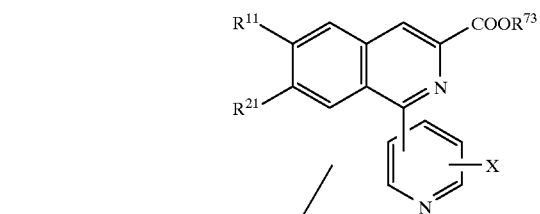

(XI)

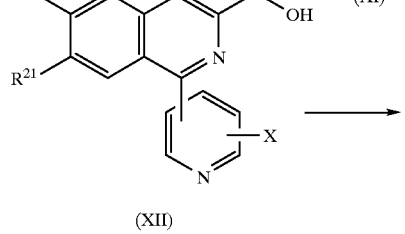

(XII)

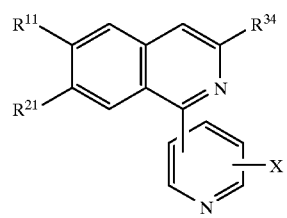

(II-a)

wherein $R^{71}$ is a lower alkyl group, $R^{72}$ is a lower alkyl group, $R^{73}$ is a lower alkyl group, $X^1$ is a halogen atom, and the other symbols are the same as defined above.

That is, the compound (II-a) is prepared by the following steps:

(i) condensing the acetal compound (VII) with the compound (VIII) to give the compound (IX);

(ii) removing the protecting groups from the compound (IX) to give the compound (X);

(iii) reacting the compound (X) with the isonitrile derivative to give the compound (XI);

(iv) subjecting the compound (XI) to reduction to give the compound (XII), (v) and if necessary, protecting the 3-hydroxymethyl group of the compound (XII) to give the compound (II-a).

Among the compounds (II), the isoquinoline compound (II-b) can be prepared as follows.

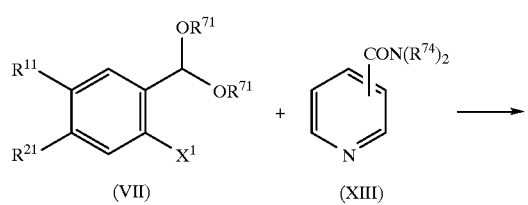

-continued

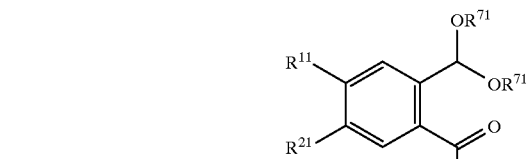

(XIV)

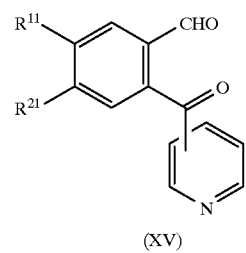

(XV)

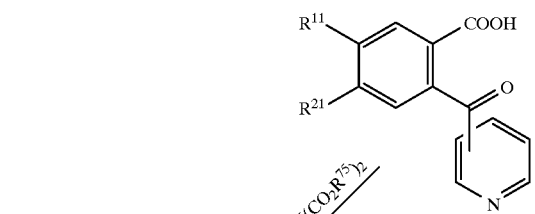

(XVI)

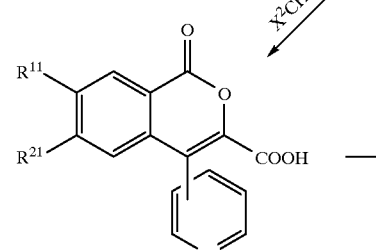

(XVII)

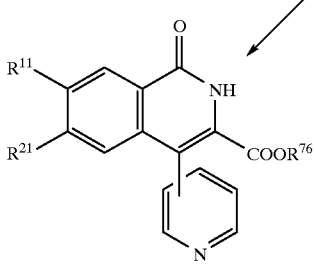

(XVIII)

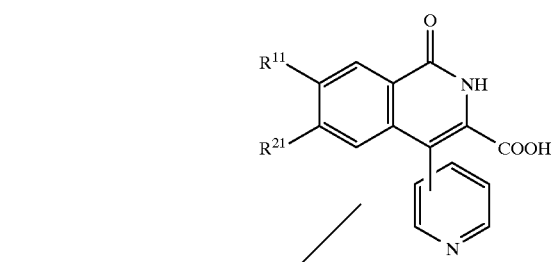

(XIX)

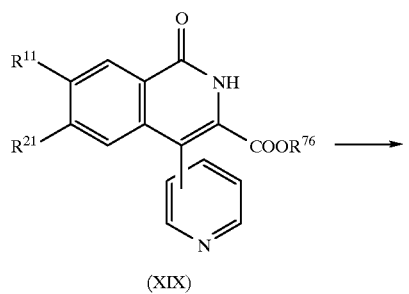

(XIX)

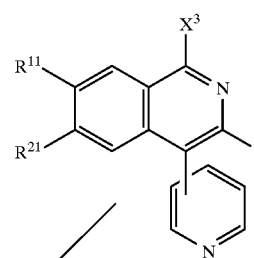

(XX)

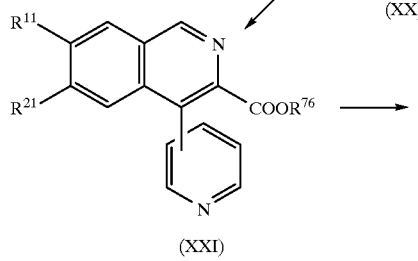

(XXI)

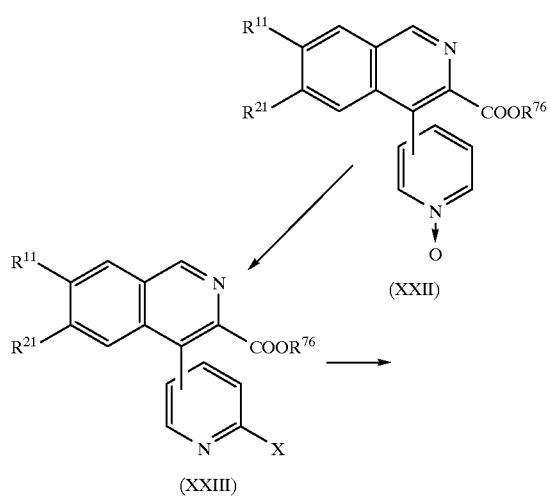

(XXIII)

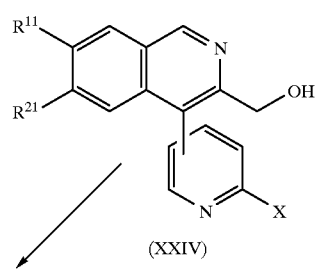

(XXIV)

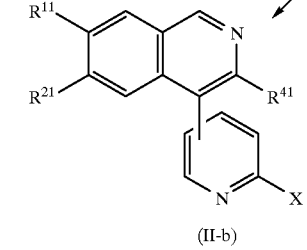

(II-b)

wherein $R^{74}$ is a lower alkyl group, $R^{75}$ is a lower alkyl group, $R^{76}$ is a lower alkyl group, $X^2$ is a halogen atom, $X^3$ is a halogen atom, and the other symbols are the same as defined above.

That is, the compound (II-b) is prepared by the following steps:

(i) condensing the acetal compound (VII) with the compound (XIII), and the protecting groups of the resulting compound (XIV) are removed;

(ii) oxidizing the resulting compound (XV);

(iii) reacting the resulting compound (XVI) with the halogenomalonic acid diester derivative;

(iv) reacting the resulting compound (XVII) with ammonia;

(v) esterifying the resulting compound (XVIII);

(vi) halogenating the resulting compound (XIX) to give the compound (XX);

(vii) de-halogenating the compound (XX) to give the compound (XXIII);

(viii) reducing the compound (XXIII) to give the compound (XXIV);

(ix) then if necessary, by protecting the 3-hydroxymethyl group of the isoquinoline nucleus of the compound (XXIV).

Among the compounds (II), the quinoline compound (II-c) can be prepared as follows.

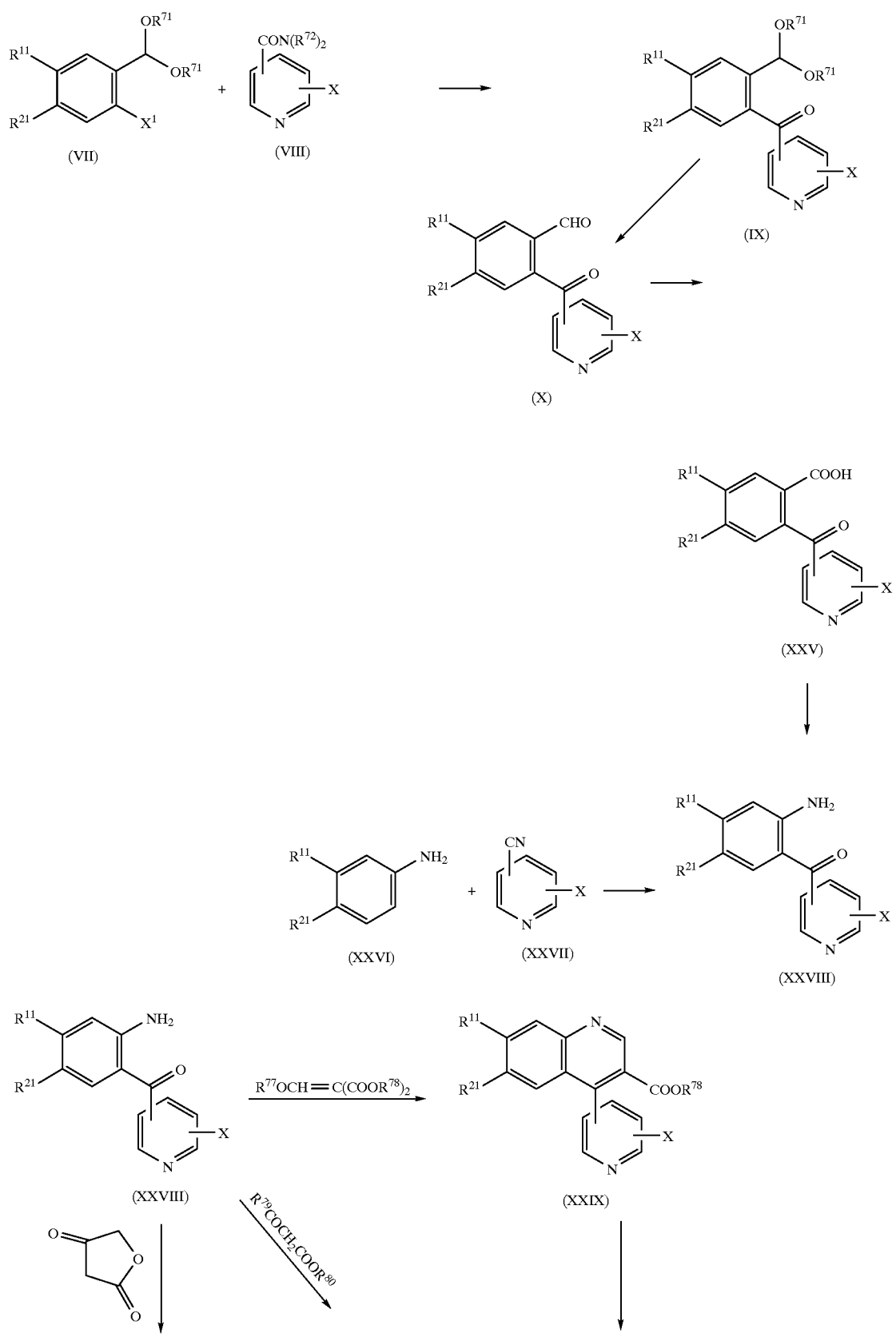

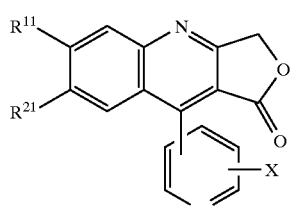
(XXXIII)

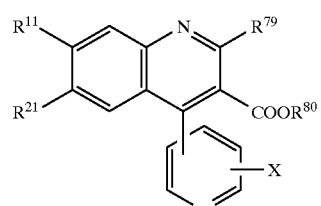
(XXXI)

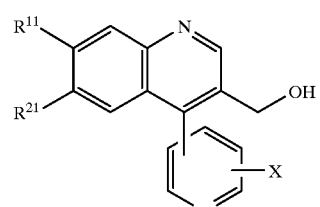
(XXX)

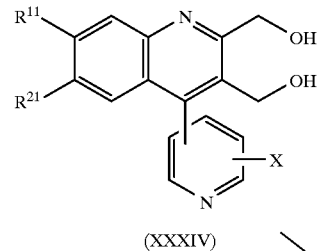
(XXXIV)

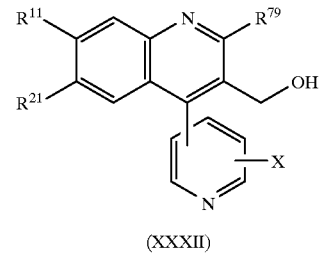
(XXXII)

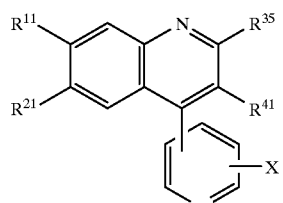
(II-c)

wherein $R^{77}$ is a lower alkyl group, $R^{78}$ is a lower alkyl group, $R^{79}$ is a lower alkyl group, $R^{80}$ is a lower alkyl group, and the other symbols are the same as defined above.

That is, the compound (II-c) is prepared by the following steps:

(i) condensing the acetal compound (VII) with the compound (VIII) to give the compound (IX);
(ii) removing the protecting groups from the compound (IX) to give the compound (X);
(iii) oxidizing the compound (X), and converting the resulting compound (XXV) into an acid azide compound, which is further subjected to rearrangement reaction to give the compound (XXVIII), or
(iv) condensing the aniline compound (XXVI) with the compound (XXVII) to give the compound (XXVIII);
(v) reacting the compound (XXVIII) with a lower alkoxymethylenemalonic acid diester compound, subjecting the resulting compound (XXIX) to reduction, to give the compound (XXX); or
(vi) alternatively, reacting the compound (XXVIII) with a 3-oxo-lower alkylcarboxylic acid ester derivative, and subjecting the resulting compound (XXXI) to reduction to give the compound (XXXII), or
(vii) alternatively, reacting the compound (XXVIII) with a tetronic acid, and subjecting the resulting compound (XXXIII) to reduction to give the compound (XXXIV);
(vii) then, if necessary, protecting the hydroxymethyl groups of the compound (XXX), the compound (XXXII) and the compound (XXXIV).

Among the compounds (II), the phthalazine compound (II-d) can be prepared as follows.

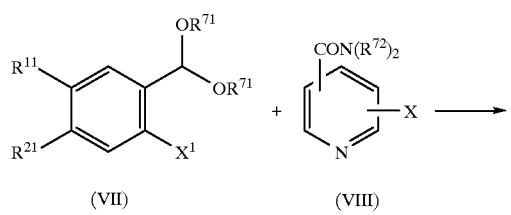
(VII)      (VIII)

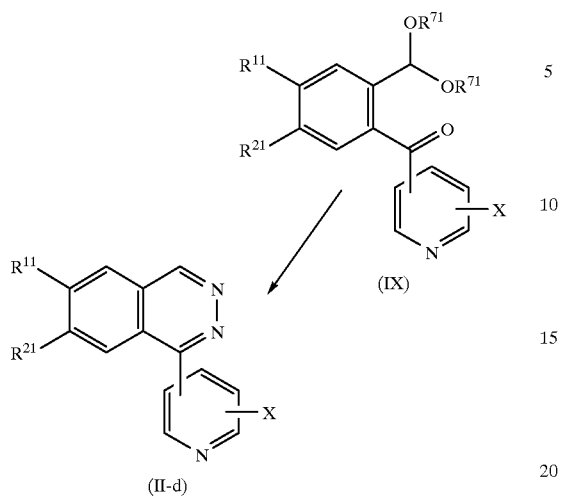

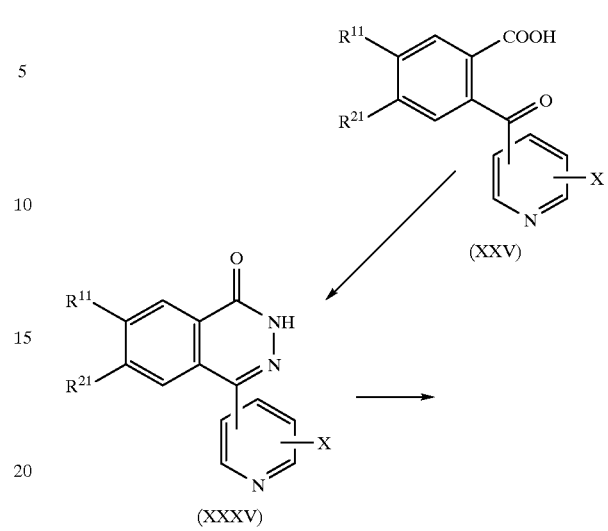

wherein the symbols are the same as defined above.

That is, the compound (II-d) may be prepared by condensing the acetal compound (VII) with the compound (VIII), removing the protecting groups from the resulting compound (IX), followed by reacting the product with hydrazine.

Among the compounds (II), the phthalazinone compound (II-e) can be prepared as follows.

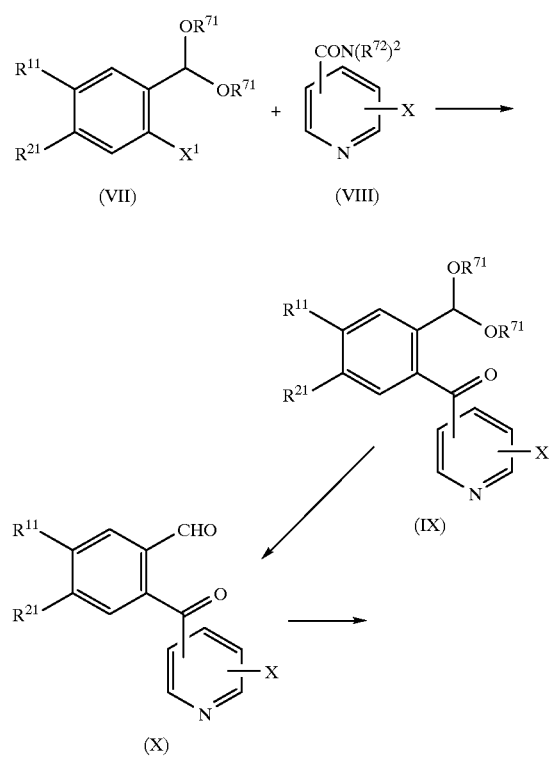

wherein the symbols are the same as defined above.

That is, the compound (II-e) is prepared by the following steps:

(i) condensing the acetal compound (VII) with the compound (VIII), (ii) removing the protecting groups from the resulting compound (IX), (iii) oxidizing the resulting compound (X) to give the compound (XXV);

(iv) reacting the compound (XXV) with hydrazine to give the compound (XXXV);

(v) then, protecting the 2-position of the phthalazine nucleus of the compound (XXXV).

The starting compound (IV) is a novel compound, and can be prepared by the following process.

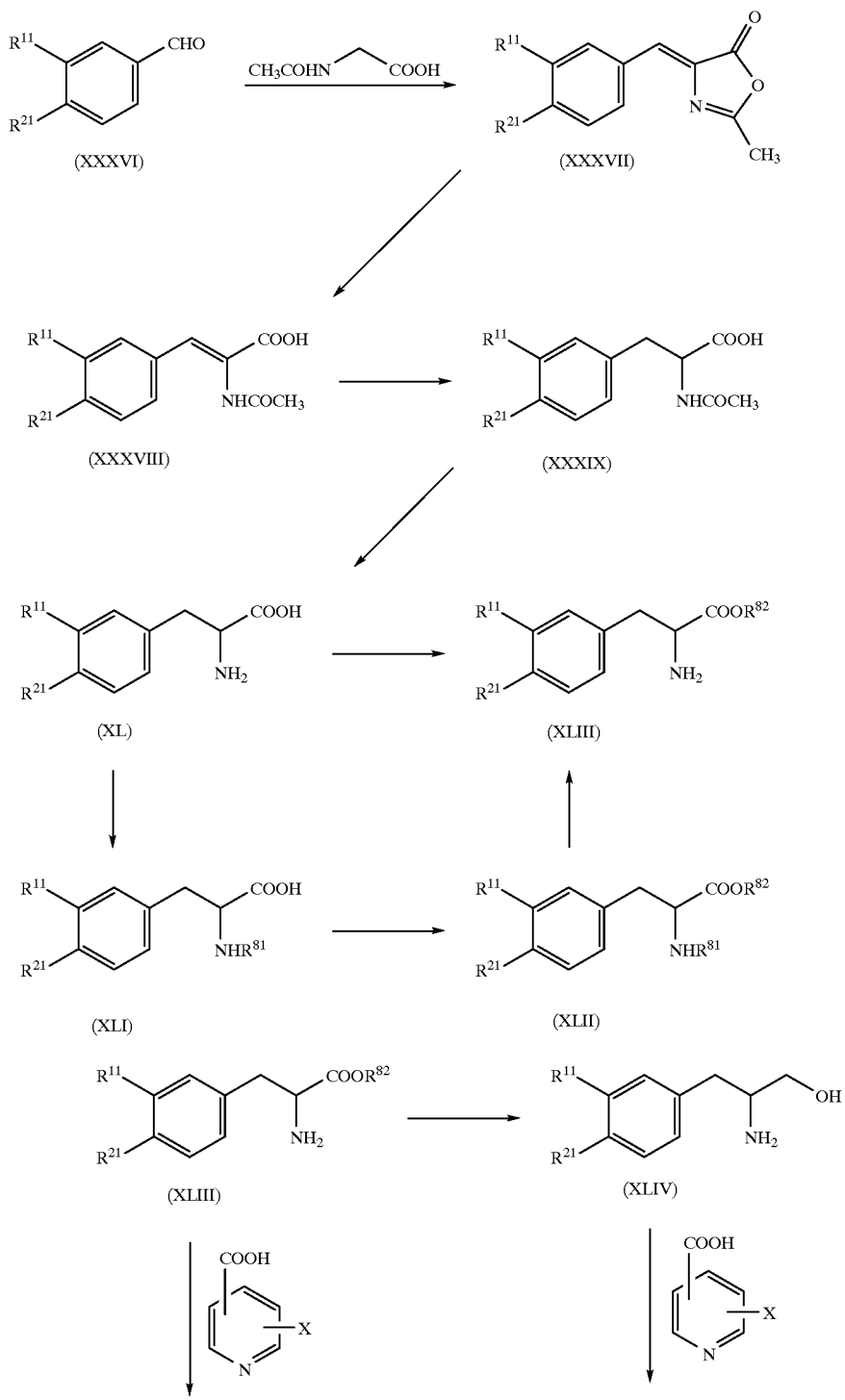

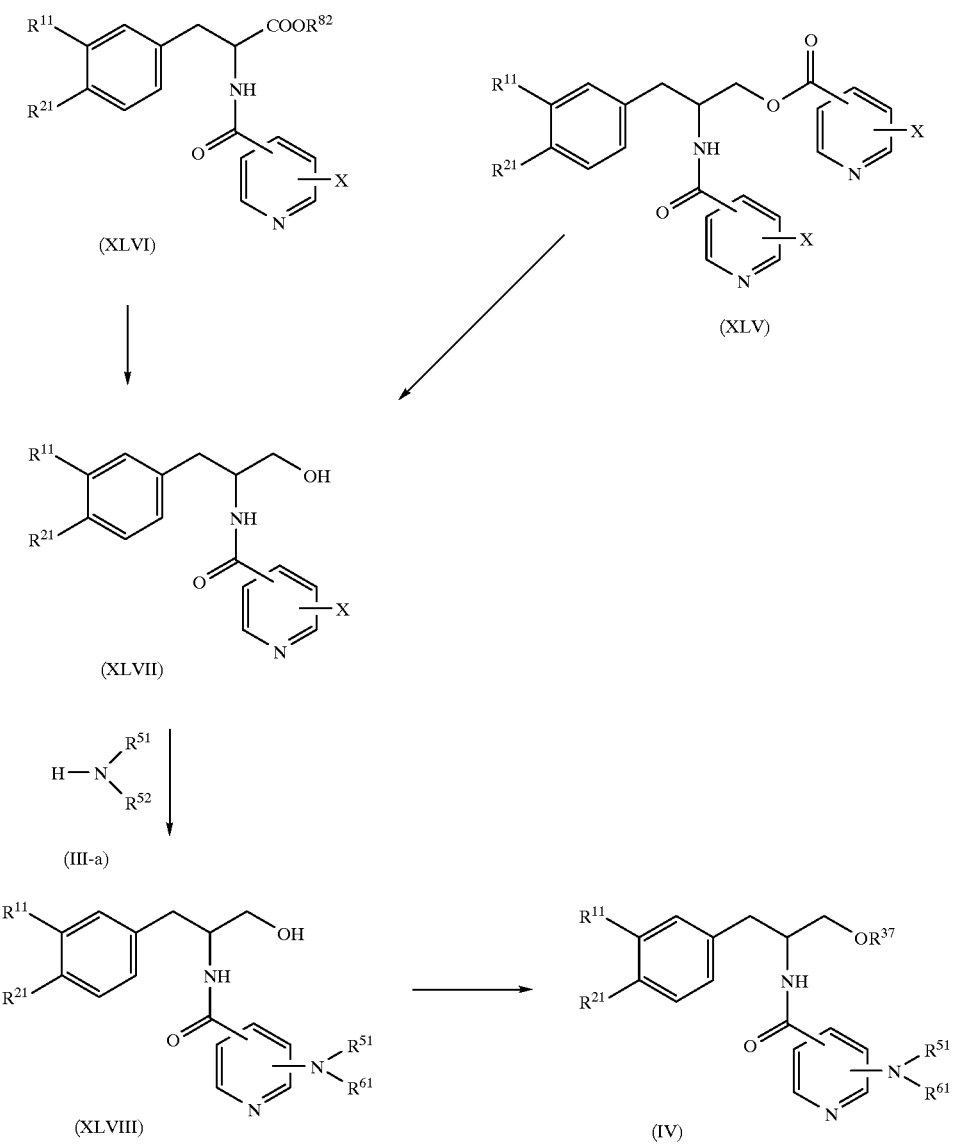

wherein $R^{81}$ is a lower alkoxycarbonyl group, $R^{82}$ is a lower alkyl group, and the other symbols are the same as defined above.

That is, the compound (IV) is prepared by the following steps:

(i) reacting the compound (XXXVI) with an N-acetylglycine to give the compound (XXXVII), (ii) hydrolyzing the compound (XXXVII) to give the compound (iii) subjecting the compound (XXXVIII) to hydrogenolysis to give the compound (XXXIX);

(iv) hydrolyzing the compound (XXXIX) to give the compound (XL);

(v) esterifying the compound (XL) to give the compound (XLIII); or (vi) alteratively protecting the amino group of the compound (XL), esterifying the resulting compound (XLI), and removing the protecting group of the amino group of the compound (XLII) to give the compound (XLIII);

(vii) subjecting the compound (XLIII) to reduction, condensing the resulting compound (XLIV) with a halogenopyridinecarboxylic acid, and hydrolyzing the resulting compound (XLV) to give the compound (XLVII); or (viii) alternatively, reacting the compound (XLIII) with the halogenopyridinecarboxylic acid, and subjecting the resulting compound (XLVI) to reduction to give the compound (XLVII);

(ix) reacting the compound (XLVII) with the compound (III-a), and if necessary, protecting the hydroxymethyl group of the resulting compound (XLVIII).

The compound of the following formula (XLIII-a) and the compound of the formula (XLIV-a) are prepared by the following process.

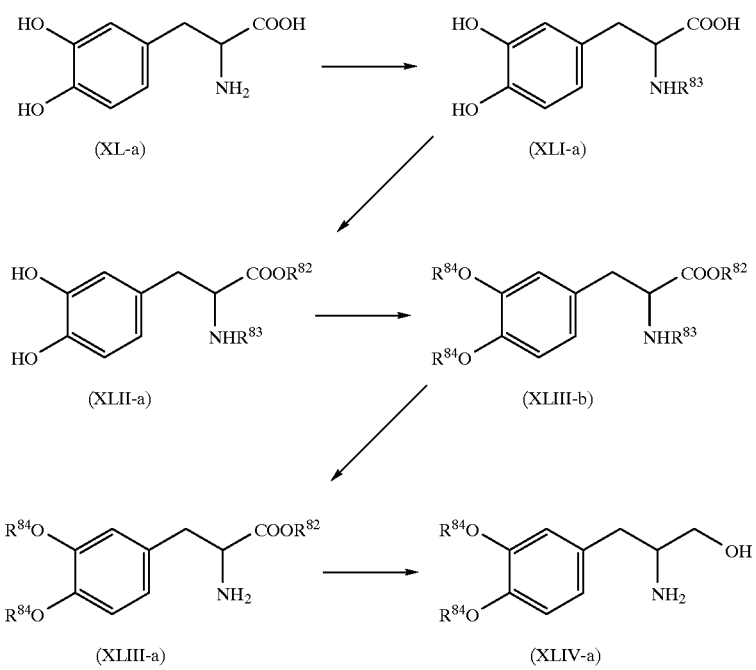

wherein $R^{83}$ is a lower alkoxycarbonyl group, $R^{84}$ is a lower alkyl group, and the other symbols are the same as defined above.

That is, the compound (XLIII-a) and the compound (XLIV-a) are obtained by the following steps:

(i) protecting the amino group of the compound (XL-a) to give the compound (XLI-a);

(ii) esterifying the compound (XLI-a) to give the compound (XLII-a);

(iii) protecting the hydroxy group of the compound (XLII-a) to give the compound (XLIII-b) (or alternatively, protecting the hydroxy moiety and the carboxyl moiety of the compound (XLI-a) are simultaneously protected to give the compound (XLIII-b));

(iv) removing the protecting groups of the amino group of the compound (XLIII-b); and further (v) subjecting the resulting compound (XLIII-a) to reduction to give the compound (XLIV-a).

In the processes for preparing the compounds (II) and (IV), each intermediate therefor can be used in the form of ones as expressed by the chemical formula per se, but also a salt thereof, or a reactive derivative thereof can be used, unless they disturb the reaction.

Moreover, in the preparation of the desired compound of the present invention and the starting compounds, when the starting compounds or each intermediate therefor have a functional group, it may be possible to protect such functional groups with a suitable protecting group other than the above-mentioned groups by a conventional method used in the synthetic chemistry field, and after these protecting groups are not necessary, then these protecting groups may be removed.

In the present specification and claims, the "alkyl group" means a straight chain or branched chain alkyl group having 1 to 16 carbon atoms, especially ones having 1 to 8 carbon atoms. The "lower alkyl group" and the "lower alkoxy group" mean a straight chain or branched chain ones having 1 to 6 carbon atoms, especially ones having 1 to 4 carbon atoms, respectively. The "lower alkanoyl group" means a straight chain or branched chain alkanoyl group having 2 to 7 carbon atoms, especially ones having 2 to 5 carbon atoms. The "cyclo-lower alkyl group" means cycloalkyl groups having 3 to 8 carbon atoms, especially ones having 3 to 6 carbon atoms. The "halogen atom" is chlorine, bromine, fluorine or iodine.

The present invention is illustrated in more detail by Examples and Reference Examples, but should not be construed to be limited thereto.

EXAMPLE 1

(1) To a solution of 4-(3-pyridyl)phthalazin-1(2H)-one (167 mg) in dimethylformamide (5 ml) are added successively potassium carbonate (103 mg), copper iodide (70 mg) and 2-bromo-4-[6,7-dimethoxy-2-(4-pyridyl)methyl-phthalazin-1(2H)-on-4-yl]pyridine (335 mg) under nitrogen atmosphere, and the mixture is refluxed for two hours. The reaction mixture is cooled, and thereto is added aqueous ammonia. The mixture is extracted with chloroform, and the extract is washed, dried, concentrated, and purified by silica gel column chromatography (solvent; chloroform:methanol=19:1) to give 4-[6,7-dimethoxy-2-(4-pyridyl)methylphthalazin-1(2H)-on-4-yl]-2-[4-(3-pyridyl)-phthalazin-1(2H)-on-2-yl]pyridine (216 mg).

(2) The compound (216 mg) obtained in the above (1) is dissolved in a mixture of chloroform and methanol (chloroform:methanol=4:1), and thereto is added 2M hydrochloric acid (0.18 ml), and the mixture is concentrated. The mixture is subjected to azeotropic distillation with ethanol, and to the residue is added chloroform. The mixture is filtered to give 4-[6,7-dimethoxy-2-(4-pyridyl)-methylphthalazin-1(2H)-on-4-yl]-2-[4-(3-pyridyl)phthalazin-1(2H)-on-2-yl]-pyridine dihydrochloride (106 mg).

M.p. 225–230° C. (decomposed)

EXAMPLES 2–5

4-(3-Pyridyl)phthalazin-1(2H)-one and the corresponding compound of the formula [II-e] are treated in the same manner as in Example 1-(1) and -(2) to give the compounds as listed in Table 1.

TABLE 1

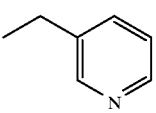

| Ex. No. | R | Physicochemical properties |
|---|---|---|
| 2** | 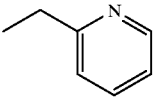 | M.p. 215–220° C. (decomp.) |
| 3** | 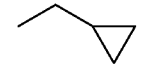 | M.p. 184–190° C. (decomp.) |
| 4* | 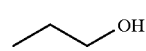 | M.p. 167–170° C. |
| 5* | ⌁⌁OH | M.p. >230° C. |

*: Hydrochloride;
**: Dihydrochloride

EXAMPLE 6

2-Bromo-4-(6,7-dimethoxyphthalazin-1-yl)pyridine and 4-(3-pyridyl)-phthalazin-1(2H)-one are treated in same manner as in Example 1-(1) and -(2) to give 4-(6,7-dimethoxyphthalazin-1-yl)-2-[4-(3-pyridyl)phthalazin-1 (2H)-on-2-yl]pyridine hydrochloride.

M.p. 232–236° C. (decomposed)

EXAMPLE 7

(1) To a solution of methyl isocyanoacetate (18 ml) in dimethylformamide (85 ml) is added sodium hydride (7.85 g, 62.4% in oil) with ice-cooling under nitrogen atmosphere, and the mixture is stirred at room temperature for 30 minutes. To a solution of 3,4-dimethoxy-6-(2-chloroisonicotinoyl)benzaldehyde (52.0 g) in dimethylformamide (170 ml) is added dropwise the above solution at 40–50° C., and then the mixture is stirred at 50° C. for one hour. The mixture is neutralized with 10% acetic acid, concentrated, and extracted with chloroform. The extract is washed, and the insoluble materials are collected by filtration, and the filtrate is dried and concentrated. The resultant and the collected insoluble materials are combined, and recrystallized from ether-methanol to give 2-chloro-4-(3-methoxycarbonyl-6,7-dimethoxyisoquinolin-1-yl) pyridine (16.1 g).

M.p. 246–247° C.

(2) The compound (12.9 g) obtained in the above (1) is suspended in tetrahydrofuran (300 ml), and thereto is added dropwise a solution of sodium bis(methoxyethoxy) aluminum hydride (21.2 ml, 70% toluene solution) in tetrahydrofuran (50 ml) at a temperature below –10° C. The mixture is gradually warmed to room temperature, and thereto is added methanol. To the mixture is added 2 M aqueous sodium hydroxide solution (90 ml), and the mixture is stirred at 40° C. for 30 minutes. The tetrahydrofuran layer is separated, and the aqueous layer is extracted with ethyl acetate. All the organic layers are combined, washed, dried, and concentrated, and the residue is purified by silica gel column chromatography (solvent; chloroform:acetone=2:1) to give 2-chloro-4-(3-hydroxymethyl-6,7-dimethoxyisoquinolin-1-yl)pyridine (7.44 g).

M.p. 162–163° C.

(3) A solution of the compound (992 mg) obtained in the above (2) and hydrazine.monohydrate (32.6 ml) is refluxed for one hour. The reaction mixture is cooled, and the precipitates are collected by filtration to give 2-hydrazino-4-(3-hydroxymethyl-6,7-dimethoxyisoquinolin-1-yl) pyridine (552 mg).

M.p. 157–159° C.

(4) A mixture of the compound (1.63 g) obtained in the above (3), 2-nicotinoylbenzoic acid (1.25 g) and ethylene glycol (50 ml) is heated with stirring at 120° C. for three hours. The reaction mixture is cooled, and thereto is added an aqueous sodium hydrogen carbonate solution. The precipitates are collected by filtration, and purified by silica gel column chromatography (solvent; chloroform:methanol= 10:1) to give 4-(3-hydroxymethyl-6,7-dimethoxyisoquinolin-1-yl)-2-[4-(3-pyridyl)phthalazin-1 (2H)-on-2-yl]pyridine (1.68 g).

M.p. >250° C.

(5) The compound (1.68 g) obtained in the above (4) is dissolved in a mixture of chloroform and methanol (chloroform:methanol=10:1), and thereto is added 2 M hydrochloric acid (1.62 ml), and the mixture is concentrated. The mixture is subjected to azeotropic distillation with ethanol, and to the residue is added ether. The precipitates are collected by filtration to give 4-(3-hydroxy-methyl-6,7-dimethoxyisoquinolin-1-yl)-2-[4-(3-pyridyl)phthalazin-1 (2H)-on-2-yl]pyridine hydrochloride (1.83 g).

M.p. 257–260° C. (decomposed)

EXAMPLES 8–13

2-Hydrazino-4-(3-hydroxymethyl-6,7-dimethoxyisoquinolin-1-yl)pyridine and the corresponding carboxylic acid compound of the formula (V) are treated in the same manner as in Example 7-(4) to give the compounds as listed in Table 2.

TABLE 2

| Ex. No. | R | Physicochemical properties |
|---|---|---|
| 8 | 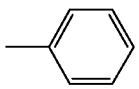 | M.p. >250° C. |
| 9 | 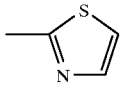 | M.p. 204–206° C. |
| 10 | —CH₃ | M.p. >250° C. |
| 11 | 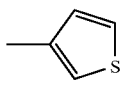 | M.p. >250° C. |
| 12 | 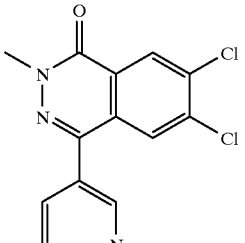 | M.p. 195–199° C. |
| 13 | —H | M.p. 248–250° C. |

EXAMPLE 14

3,4-Diethoxy-6-(2-chloroisonicotinoyl)benzaldehyde is treated in the same manner as in Example 7-(1) to -(5) to give 4-(3-hydroxymethyl-6,7-diethoxyisoquinolin-1-yl)-2-[4-(3-pyridyl)phthalazin-1(2H)-on-2-yl]pyridine hydrochloride.

M.p. >250° C.

EXAMPLES 15–17

2-Hydrazino-4-(3-hydroxymethyl-6,7-diethoxyisoquinolin-1-yl)pyridine and the corresponding carboxylic acid compound of the formula (V) are treated in the same manner as in Example 7-(4) to -(5) to give the compounds as listed in Table 3.

TABLE 3

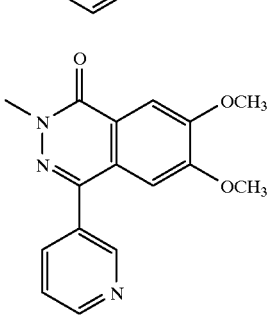

| Ex. No. | R | Physicochemical properties |
|---|---|---|
| 15 | 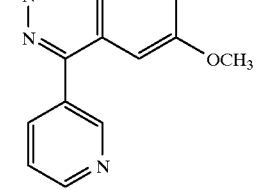 | M.p. >250° C. |
| 16 | 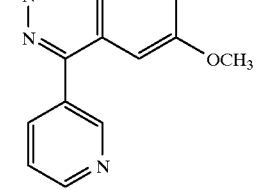 | M.p. >250° C. |
| 17 | 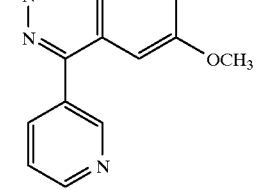 | M.p. 208–212° C. (decomp.) |

EXAMPLE 18

2-Hydrazino-4-(3-hydroxymethyl-6,7-diethoxyisoquinolin-1-yl)pyridine and 2-(3,4,5-trimethoxybenzoyl)-3-thiophenecarboxylic acid are treated in the same manner as in Example 7-(4) to give 4-(3-hydroxymethyl-6,7-diethoxyisoquinolin-1-yl)-2-[7-(3,4,5-trimethoxyphenyl)thieno[2,3-d]pyridazin-4(5H)-on-5-yl]pyridine.

M.p. 250–251° C.

EXAMPLE 19

(1) To acetic acid (80 ml) are added 4-(1-chloro-6,7-dimethoxy-3-methoxycarbonylisoquinolin-4-yl)pyridine (6.11 g), sodium acetate (1.4 g) and 10% palladium-carbon (2.5 g), and the mixture is subjected to hydrogenation at 50° C. for 19 hours under pressure (2.7 atm). The palladium-carbon is removed by filtration, and the filtrate is concentrated to give 4-(6,7-dimethoxy-3-methoxycarbonylisoquinolin-4-yl)pyridine (4.84 g).

M.p. 168–170° C. (decomposed)

(2) To a solution of the compound (4.4 g) obtained in the above (1) in methylene chloride (40 ml) is added m-chloroperbenzoic acid (5.1 g) at 0° C., and the mixture is stirred at 0° C. for two hours, and stirred at room temperature for 40 hours. To the reaction mixture is added an aqueous sodium thiosulfate solution, and the mixture is extracted with chloroform. The extract is washed, dried, and concentrated. The residue is purified by silica gel column chromatography (solvent; chloroform:methanol=20:1) to give 4-(6,7-dimethoxy-3-methoxycarbonylisoquinolin-4-yl) pyridine.N-oxide 2.12 g).

M.p. 220–224° C. (decomposed)

(3) To the compound (2.07 g) obtained in the above (2) is added phosphorus oxychloride (20 ml), and the mixture is refluxed for one hour. The reaction mixture is concentrated, and to the residue is added chloroform. To the mixture is added an aqueous sodium hydrogen carbonate solution, and the mixture is extracted with chloroform. The extract is washed, dried, and concentrated, and the residue is purified by silica gel column chromatography (solvent; chloroform:ethyl acetate=10:1) to give 2-chloro-4-(6,7-dimethoxy-3-methoxycarbonylisoquinolin-4-yl)pyridine (1.05 g).

M.p. 164–168° C. (decomposed)

(4) The compound obtained in the above (3) is treated in the same manner as in Example 7-(2) to -(5) to give 4-(6,7-dimethoxy-3-hydroxymethylisoquinolin-4-yl)-2-[4-(3-pyridyl)phthalazin-1(2H)-on-2-yl]pyridine hydrochloride (145 mg).

M.p. 231–233° C. (decomposed)

EXAMPLE 20

(1) To a solution of (2S)-1-acetoxy-3-(3,4-dimethoxyphenyl)-2-{2-[4-(3-pyridyl)phthalazin-1(2H)-on-2-yl]isonicotinoylamino}propane (150 mg) in acetonitrile (5 ml) is added phosphorus oxychloride (0.29 ml), and the mixture is heated under reflux overnight. The reaction mixture is cooled to room temperature, and neutralized with an aqueous sodium hydrogen carbonate solution. The mixture is extracted with chloroform, and the extract is washed, dried, and concentrated. The residue is crystallized from ethyl acetate to give (3S)-4-(3-acetoxymethyl-3,4-dihydro-6,7-dimethoxyisoquinolin-1-yl)-2-[4-(3-pyridyl)phthalazin-1(2H)-on-2-yl]pyridine (136 mg), as yellow crystals.

M.p. 177–179° C.

(2) The compound (200 mg) obtained in the above (1) is added to a 4 M solution of hydrogen chloride in dioxane (0.09 ml) to give (3S)-4-(3-acetoxymethyl-3,4-dihydro-6,7-dimethoxyisoquinolin-1-yl)-2-[4-(3-pyridyl)-phthalazin-1(2H)-on-2-yl]pyridine hydrochloride (200 mg).

M.p. 178–181° C. (decomposed)

EXAMPLES 21–32

The corresponding compounds (IV) are treated in the same manner as in Example 20-(1) and -(2), or Example 20-(1) to give the compounds as listed in Tables 4–6.

TABLE 4

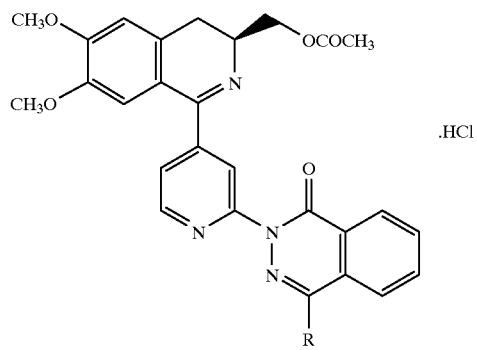

| Ex. No. | R | Physicochemical properties |
|---|---|---|
| 21 | pyrimidin-5-yl | M.p. 155–158° C. (decomp.) |
| 22 | pyridin-2-yl | M.p. 157–159° C. (decomp.) |
| 23 | 4-(N,N-dimethylamino)phenyl | M.p. 165–167° C. (decomp.) |
| 24 | pyridin-3-yl | M.p. 142–145° C. (decomp.) |

TABLE 5

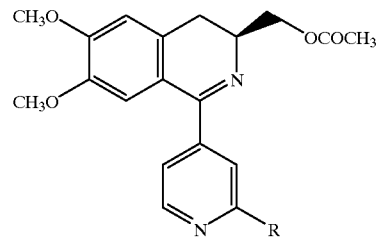

| Ex. No. | R | Physicochemical properties |
|---|---|---|
| 25 | 5-(2-morpholinoethoxy)-1-methyl-isoquinolin-1(2H)-on-... | M.p. 99–102° C. (decomp.) |

TABLE 5-continued

[Structure: 6,7-dimethoxy-3-(acetoxymethyl)-1-(2-R-pyridin-4-yl)-3,4-dihydroisoquinoline]

| Ex. No. | R | Physicochemical properties |
|---|---|---|
| 26 | [1-methyl-4-(pyridin-4-yl)quinolin-2(1H)-one] | M.p. 229–230° C. |
| 27 | [2-methyl-5-(pyridin-3-ylmethoxy)isoquinolin-1(2H)-one] | M.p. 201–204° C. |
| 28 | [1-methyl-4-(pyridin-2-yl)pyridin-2(1H)-one] | M.p. 184–186° C. |

TABLE 6

[Structure: 6,7-diethoxy-3-(acetoxymethyl)-1-(2-R-pyridin-4-yl)-3,4-dihydroisoquinoline]

| Ex. No. | R | Physicochemical properties |
|---|---|---|
| 29 | [2-methyl-4-(pyridin-3-yl)phthalazin-1(2H)-one] | M.p. 208–210° C. |
| 30 | [1,3-dimethylquinazoline-2,4(1H,3H)-dione] | M.p. 220–223° C. |
| 31 | [3-methylquinazolin-4(3H)-one] | M.p. 175–177° C. |
| 32 | [1-methyl-1,6-naphthyridin-2(1H)-one] | M.p. 186–188° C. |

EXAMPLE 33

(1) (3S)-4-(3-Acetoxymethyl-3,4-dihydro-6,7-dimethoxyisoquinolin-1-yl)-2-[4-(3-pyridyl)phthalazin-1(2H)-on-2-yl]pyridine (400 mg) is suspended in a mixture of methanol (20 ml) and tetrahydrofuran (10 ml), and thereto is added dropwise a 1 M aqueous lithium hydroxide solution (1.43 ml) under ice-cooling. The mixture is stirred for 15 minutes under ice-cooling, and the mixture is reacted at room temperature for three hours. The reaction mixture is concentrated, and the water is added to the residue. The mixture is extracted with methylene chloride, and the extract is washed, dried and concentrated. The reside is purified by silica gel column chromatography (solvent; chloroform:methanol=10:1) to give (3S)-4-(3,4-dihydro-3-hydroxymethyl-6,7-dimethoxyisoquinolin-1-yl)-2-[4-(3-pyridyl)phthalazin-1(2H)-on-2-yl]pyridine (230 mg).

M.p. 235–238° C.

(2) The compound (200 mg) obtained in the above (1) is reacted with a 4 M solution of hydrogen chloride in dioxane (0.1 ml) to give (3S)-4-(3,4-dihydro-3-hydroxymethyl-6,7-dimethoxyisoquinolin-1-yl)-2-[4-(3-pyridyl)-phthalazin-1(2H)-on-2-yl]pyridine hydrochloride (200 mg).

M.p. 225–228° C. (decomposed)

EXAMPLES 34–45

4-(3-Acetoxymethyl-3,4-dihydro-6,7-di-lower alkoxyisoquinolin-1-yl)-2-substituted pyridine compounds are treated in the same manner as in Example 33-(1) and -(2) to give the compounds as listed in Tables 7 to 9.

TABLE 7

| Ex. No. | R | Physicochemical properties |
|---|---|---|
| 34 | 4-pyrimidinyl | M.p. 249–251° C. (decomp.) |
| 35 | 2-pyridyl | M.p. 213–216° C. (decomp.) |
| 36 | 4-(N,N-dimethylamino)phenyl | M.p. 182–185° C. (decomp.) |

TABLE 7-continued

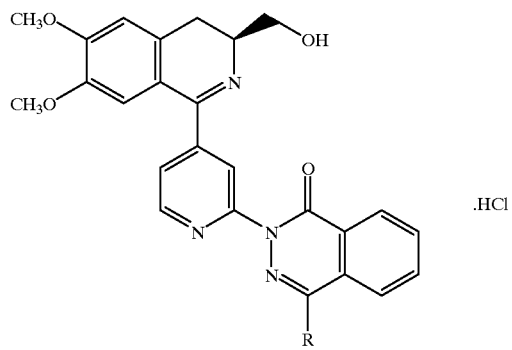

| Ex. No. | R | Physicochemical properties |
|---|---|---|
| 37 | 3-ethylpyridyl | M.p. 171–173° C. (decomp.) |

TABLE 8

| Ex. No. | R | Physicochemical properties |
|---|---|---|
| 38 | N-methyl-4-(2-morpholinoethoxy)isoquinolin-1(2H)-one | M.p. 140–143° C. (decomp.) |
| 39 | 1-methyl-4-(4-pyridyl)quinolin-2(1H)-one | M.p. 215–217° C. (decomp.) |

TABLE 8-continued

[Structure: 6,7-dimethoxy-3-hydroxymethyl-3,4-dihydroisoquinoline with 1-(2-R-pyridin-4-yl) substituent] .HCl

| Ex. No. | R | Physicochemical properties |
|---|---|---|
| 40 | [1-methyl-5-(pyridin-3-ylmethoxy)isoquinolin-1(2H)-on-yl] | M.p. 207–210° C. (decomp.) |
| 41 | [1-methyl-4-(pyridin-2-yl)pyridin-2(1H)-on-yl] | M.p. 205–207° C. (decomp.) |

TABLE 9

[Structure: 6,7-diethoxy-3-hydroxymethyl-3,4-dihydroisoquinoline with 1-(2-R-pyridin-4-yl) substituent] .HCl

| Ex. No. | R | Physicochemical properties |
|---|---|---|
| 42 | [2-methyl-4-(pyridin-3-yl)phthalazin-1(2H)-on-yl] | M.p. 243–245° C. (decomp.) |
| 43 | [1,3-dimethylquinazoline-2,4-dione-yl] | M.p. 235–236° C. (decomp.) |
| 44 | [3-methylquinazolin-4(3H)-on-yl] | M.p. 244–246° C. (decomp.) |
| 45 | [1-methyl-2,6-naphthyridin-2(1H)-on-yl] | M.p. 203–206° C. (decomp.) |

EXAMPLE 46

1-Acetoxy-3-(3,4-dimethoxyphenyl)-2-{2-[4-(3-pyridyl)phthalazin-1(2H)-on-2-yl]isonicotinoylamino}propane is treated in the same manner as in Example 20-(1) and -(2) to give 4-(3-acetoxymethyl-3,4-dihydro-6,7-dimethoxyisoquinolin-1-yl)-2-[4-(3-pyridyl)phthalazin-1(2H)-on-2-yl]pyridine hydrochloride.

M.p. 183–186° C. (decomposed)

EXAMPLE 47

4-(3-Acetoxymethyl-3,4-dihydro-6,7-dimethoxyisoquinolin-1-yl)-2-[4-(3-pyridyl)phthalazin-1(2H)-on-2-yl]pyridine is treated in the same manner as in Example 33-(1) and -(2) to give 4-(3,4-dihydro-3-hydroxymethyl-6,7-dimethoxyisoquinolin-1-yl)-2-[4-(3-pyridyl)phthalazin-1(2H)-on-2-yl]pyridine hydrochloride.

M.p. 236–238° C. (decomposed)

EXAMPLE 48

2-Hydroxymethyl-4-(4-pyridyl)-6,7-dimethoxy-3-quinolinecarboxylic lactone (14 g) is suspended in tetrahydrofuran (50 ml), and thereto is added dropwise a mixture of sodium bis(methoxyethoxy)aluminum hydride (20.3 ml, 70% toluene solution) in tetrahydrofuran (10 ml) at −10° C.

over a period of 30 minutes. The mixture is stirred at −10° C. for 1.5 hour, and stirred at 0° C. for 6 hours. To the mixture is added methanol, and then further added thereto a 2 M aqueous sodium hydroxide solution (100 ml) at 0° C. The mixture is evaporated to remove the tetrahydrofuran, and the residue is extracted with methylene chloride. The extract is washed, dried, and concentrated. The residue is purified by silica gel column chromatography (solvent; chloroform:methanol=20:1) to give 4-[2,3-bis(hydroxymethyl)-6,7-dimethoxyquinolin-4-yl]pyridine (5.12 g).

M.p. 197–200° C.

EXAMPLE 49

2-Chloro-4-[2,3-bis(hydroxymethyl)-6,7-dimethoxyquinolin-4-yl]-pyridine is treated in the same manner as in Example 7-(3) to give 2-hydrazino-4-[2,3-bis(hydroxymethyl)-6,7-dimethoxyquinolin-4-yl]pyridine.

M.p. 225–227° C.

EXAMPLE 50

2-Hydrazino-4-[2,3-bis(hydroxymethyl)-6,7-dimethoxyquinolin-4-yl]-pyridine is treated in the same manner as in Example 7-(4) and -(5) to give 4-[2,3-bis(hydroxymethyl)-6,7-dimethoxyquinolin-4-yl]-2-[4-(3-pyridyl)-phthalazin-1(2H)-on-2-yl]pyridine hydrochloride.

M.p. 216–219° C. (decomposed)

EXAMPLE 51

(1) A mixture of 3,4-dimethoxy-6-(2-chloroisonicotinoyl)aniline (2.93 g), methyl acetoacetate (2.16 ml), conc. hydrochloric acid (0.1 ml) and acetic acid (30 ml) is heated under reflux for two hours. The reaction mixture is cooled to room temperature, and thereto is added an aqueous sodium hydrogen carbonate solution. The mixture is extracted with ethyl acetate, and the extract is washed, dried, and concentrated. The residue is purified by silica gel column chromatography (solvent; chloroform:ethyl acetate=9:1) to give 2-chloro-4-(6,7-dimethoxy-3-methoxycarbonyl-2-methylquinolin-4-yl)pyridine (3.0 g).

M.p. 145–147° C.

(2) 2-Chloro-4-(6,7-dimethoxy-3-methoxycarbonyl-2-methylquinolin-4-yl)pyridine is treated in the same manner as in Example 7-(2) to -(5) to give 4-(3-hydroxymethyl-6,7-dimethoxy-2-methylquinolin-4-yl)-2-[4-(3-pyridyl)-phthalazin-1(2H)-on-2-yl]pyridine hydrochloride.

M.p. >250° C.

EXAMPLE 52

(1) 2-Chloro-4-(3-hydroxymethyl-6,7-dimethoxyquinolin-4-yl)pyridine is treated in the same manner as in Example 7-(3) to give 2-hydrazino-4-(3-hydroxymethyl-6,7-dimethoxyquinolin-4-yl)pyridine.

M.p. 217–220° C.

(2) The compound obtained in the above (1) is treated in the same manner as in Example 7-(4) and -(5) to give 4-(3-hydroxymethyl-6,7-dimethoxyquinolin-4-yl)-2-[4-(3-pyridyl)phthalazin-1(2H)-on-2-yl]pyridine hydrochloride.

M.p. >250° C.

Reference Example 1

To a solution of 2-bromo-4,5-dimethoxybenzaldehyde dimethyl acetal (21.8 g) in tetrahydrofuran (80 ml) is added dropwise a solution of n-butyl lithium (1.6 M hexane solution, 46.8 ml) at a temperature below −50° C. under nitrogen atmosphere, and the mixture is stirred for 20 minutes. The resulting solution is added dropwise into a solution of 2-bromo-N,N-dimethylisonicotinamide (18.1 g) in tetrahydrofuran (80 ml) at a temperature below −60° C., and the mixture is stirred for 30 minutes. To the reaction mixture is added acetic acid (4.5 ml), and the mixture is poured into water, and extracted with ethyl acetate. The extract is washed, dried, and concentrated, and the residue is purified by silica gel column chromatography (solvent; hexane:ethyl acetate=2:1) to give 3,4-dimethoxy-6-(2-bromoisonicotinoyl)benzaldehyde dimethyl acetal (13.9 g) as an oily product.

Reference Example 2

3,4-Dimethoxy-6-(2-bromoisonicotinoyl)benzaldehyde dimethyl acetal (13.9 g) and 2 M hydrochloric acid (1 ml) are added to a mixture of acetone (30 ml) and water (5 ml), and the mixture is stirred at room temperature for two hours. The mixture is evaporated to remove the acetone, and the remaining aqueous layer is extracted with chloroform. The extract is washed, dried, and concentrated. The residue is purified by silica gel column chromatography (solvent; chloroform:ethyl acetate=4:1) to give 3,4-dimethoxy-6-(2-bromoisonicotinoyl)benzaldehyde (8.65 g).

M.p. 133–134° C.

Reference Example 3

To a solution of 3,4-dimethoxy-6-(2-bromoisonicotinoyl)benzaldehyde (8.61 g) in dioxane (120 ml) is added dropwise a solution of resorcinol (3.25 g) in acetate buffer (pH 3.8, 60 ml) at room temperature. To the mixture is Gradually added dropwise an aqueous solution of sodium hypochlorite (3.1 g) in water (30 ml), and the mixture is stirred at room temperature for two hours. The pH value of the reaction mixture is adjusted to about pH 1 with conc. hydrochloric acid, and then extracted with chloroform. The extract is washed, dried, and concentrated to give 3,4-dimethoxy-6-(2-bromoisonicotinoyl)benzoic acid (8.07 g).

M.p. 199–200° C.

Reference Example 4

3,4-Dimethoxy-6-(2-bromoisonicotinoyl)benzoic acid (15.2 g) and hydrazine monohydrate (15 ml) are added to ethanol (30 ml), and the mixture is heated under reflux for one hour. The reaction mixture is cooled with ice, and the precipitates are collected by filtration to give 2-bromo-4-(6,7-dimethoxyphthalazin-1(2H)-on-4-yl)pyridine (14.1 g).

M.p. >230° C.

Reference Example 5

2-Bromo-4-(6,7-dimethoxyphthalazin-1(2H)-on-4-yl)pyridine (362 mg), 4-picolyl chloride hydrochloride (180 mg), and potassium carbonate (359 mg) are added to dimethylformamide (10 ml), and the mixture is heated with stirring at 80° C. for three hours under nitrogen atmosphere. Water is added to the reaction mixture, and the mixture is extracted with methylene chloride. The extract is washed, dried, and concentrated to give 2-bromo-4-[6,7-dimethoxy-2-(4-pyridyl)methylphthalazin-1(2H)-on-4-yl]pyridine (355 mg).

M.p. 182–184° C.

Reference Examples 6–8

2-Bromo-4-(6,7-dimethoxyphthalazin-1(2H)-on-4-yl) pyridine and the corresponding halogeno compound are treated in the same manner as in Reference Example 5 to give the compounds as listed in Table 10.

TABLE 10

[Structure: 6,7-dimethoxyphthalazin-1(2H)-one with N-R substituent and 4-(2-bromopyridin-4-yl) group]

| Ref. Ex. No. | R | Physicochemical properties |
|---|---|---|
| 6 | -CH₂-(pyridin-3-yl) | M.p. 189–191° C. |
| 7 | -CH₂-(pyridin-2-yl) | M.p. 197–199° C. |
| 8 | -CH₂-cyclopropyl | M.p. 213–215° C. |

Reference Example 9

To a solution of 2-bromo-4-(6,7-dimethoxyphthalazin-1 (2H)-on-4-yl)pyridine (362 mg) in dimethylformamide (2 ml) is added sodium hydride (48 mg, 62.4% in oil,) with ice-cooling under nitrogen atmosphere, and the mixture is stirred at room temperature for 30 minutes. To the mixture is methyl bromoacetate (0.11 ml) under ice-cooling, and the mixture is stirred for 15 minutes. To the mixture is added water, and the mixture is extracted with ethyl acetate. The extract is washed, dried, and concentrated to give 2-bromo-4-(6,7-dimethoxy-2-methoxycarbonylmethylphthalazin-1 (2H)-on-4-yl)pyridine (390 mg).

M.p. 200–201° C.

Reference Example 10

To a solution of 2-bromo-4-(6,7-dimethoxy-2-methoxycarbonylmethylphthalazin-1(2H)-on-4-yl)pyridine (4.34 g) in tetrahydrofuran (20 ml) is added sodium borohydride (0.76 g), and further thereto is added dropwise with heating a mixture of methanol (3.2 ml) and tetrahydrofuran (5 ml) under reflux over a period of one hour. The reaction mixture is allowed to stand for cooling, and thereto is added water under ice-cooling. The mixture is extracted with chloroform, and the extract is washed, dried and concentrated. The residue is recrystallized from isopropyl ether to give 2-bromo-4-(6,7-dimethoxy-2-hydroxyethylphthalazin-1(2H)-on-4-yl)pyridine (3.08 g).

M.p. 208–210° C.

Reference Example 11

To a solution of 3,4-dimethoxy-6-(2-bromoisonicotinoyl) benzaldehyde (4.5 g) in methanol (70 ml) is added dropwise hydrazine monohydrate (0.8 ml). The reaction mixture is cooled with ice, and the precipitates are collected by filtration, and recrystallized from methanol to give 2-bromo-4-(6,7-dimethoxyphthalazin-1-yl)pyridine (4.01 g) as yellow crystals.

M.p. 157–159° C.

Reference Example 12

2-Bromo-4,5-dimethoxybenzaldehyde dimethyl acetal and 2-chloro-N,N-dimethylisonicotineamide are treated in the same manner as in Reference Example 1 to give 3,4-dimethoxy-6-(2-chloroisonicotinoyl)benzaldehyde dimethyl acetal as an oily product.

Reference Example 13

2-Bromo-4,5-diethoxybenzaldehyde dimethyl acetal and 2-chloro-N,N-dimethylisonicotineamide are treated in the same manner as in Reference Examples 1 and 2 to give 3,4-diethoxy-6-(2-chloroisonicotinoyl)benzaldehyde.

M.p. 153–154° C.

Reference Example 14

2-Bromo-4,5-dimethoxybenzaldehyde dimethyl acetal and N,N-dimethylisonicotineamide are treated in the same manner as in Reference Examples 1 and 2 to give 3,4-dimethoxy-6-(2-isonicotinoyl)benzaldehyde.

M.p. 128–130° C.

Reference Example 15

3,4-Dimethoxy-6-(2-isonicotinoyl)benzaldehyde is treated in the same manner as in Reference Example 3 to give 3,4-dimethoxy-6-(2-isonicotinoyl)benzoic acid.

M.p. 258–260° C. (decomposed)

Reference Example 16

(1) To a solution of 3,4-dimethoxy-6-(2-isonicotinoyl) benzoic acid (50.8 g) and diethyl bromomalonate (30 ml) in dimethylformamide (500 ml) is added potassium carbonate (24 g), and the mixture is stirred at room temperature for four hours. The mixture is concentrated under reduced pressure to remove the solvent, and to the residue is poured water. The mixture is extracted with ethyl acetate, and the extract is washed, dried, and concentrated. The residue is crystallized from ether. The resulting crystals are added to a mixture of acetic acid (300 ml) and conc. hydrochloric acid (300 ml). The mixture is heated under reflux for five hours, and concentrated. The residue is crystallized from tetrahydrofuran to give 3-carboxy-4-(4-pyridyl)-6,7-dimethoxyisocoumarin (23.4 g).

M.p. >250° C.

(2) To a 2.6 M ammonia in methanol (100 ml) is added 3-carboxy-4-(4-pyridyl)-6,7-dimethoxyisocoumarin (1.86 g), and the mixture is allowed to stand for five days at room temperature in a pressure bottle. The reaction mixture is concentrated, and thereto is added water. The pH value of the mixture is adjusted to about pH 5 with 1 M hydrochloric acid, and concentrated. To the residue is added a 4 M hydrogen chloride in ethyl acetate, and the mixture is stirred at room temperature for 20 hours. The reaction mixture is concentrated, and the residue is dissolved in a mixture of methanol and chloroform (3:2), and the mixture is washed with a saturated sodium chloride solution, dried, and concentrated. The residue is recrystallized from methanol-ethyl acetate to give 3-carboxy-4-(4-pyridyl)-6,7-dimethoxyisoquinolin-1(2H)-one hydrochloride (1.3 g).

M.p. >250° C.

(3) 3-Carboxy-4-(4-pyridyl)-6,7-dimethoxyisoquinolin-1 (2H)-one hydrochloride (12.6 g) is added to phosphorus oxychloride (200 mg), and the mixture is stirred at 50° C. for 1.5 hour. The reaction mixture is concentrated, and thereto is added toluene (200 ml), and thereto is further added methanol (100 ml). To the mixture is further added triethylamine (15 ml) at 0° C., and the mixture is stirred at room temperature for 30 minutes. The reaction solution is concentrated, and to the residue is added water. The mixture is extracted with chloroform, and the extract is washed, dried, and concentrated. The residue is purified by silica gel chromatography (solvent; chloroform:ethyl acetate=5:1) to give 3-methoxycarbonyl-4-(4-pyridyl)-6,7-dimethoxyisoquinolin-1(2H)-one (6.55 g).

M.p. 243–245° C. (decomposed)

(4) To phosphorus oxychloride (100 ml) is added 3-methoxycarbonyl-4-(4-pyridyl)-6,7-dimethoxyisoquinolin-1(2H)-one (6 g), and the mixture is heated under reflux for 2.5 hours. The reaction mixture is concentrated, and thereto is added chloroform. To the mixture is further added gradually a saturated aqueous sodium hydrogen carbonate solution, and the mixture is stirred for 20 minutes. The organic layer is collected, dried, and concentrated. The residue is purified by silica gel chromatography (solvent; chloroform:ethyl acetate=5:1) to give 1-chloro-3-methoxycarbonyl-4-(4-pyridyl)-6,7-dimethoxyisoquinoline (5.17 g).

M.p. 220–222° C. (decomposed)

Reference Example 17

(1) To a suspension of lithium aluminum hydride (7.75 g) in tetrahydrofuran (200 ml) is gradually added dropwise a solution of 3-(3,4-dimethoxyphenyl)-L-alanine methyl ester (12.2 g) in tetrahydrofuran (100 ml) at 0° C. The reaction mixture is stirred at 0° C. for 30 minutes, and then thereto are added dropwise water (7.7 ml), 10% aqueous sodium hydroxide solution (7.7 ml) and water (23.1 ml). The reaction mixture is stirred at room temperature overnight, and filtered through a cerite pad. The filtrate is concentrated to give (2S)-2-amino-3-(3,4-dimethoxyphenyl)-1-propanol (10.8 g) as an brown oily product.

(2) (2S)-2-Amino-3-(3,4-dimethoxyphenyl)-1-propanol (2 g), 2-bromo-isonicotinic acid (4.2 g), 1-hydroxybenzotriazole monohydrate (3.16 g) and 1,3-dicyclohexylcarbodiimide (4.26 g) are added to methylene chloride (20 ml), and the mixture is stirred at room temperature overnight. The reaction mixture is concentrated, and thereto is added ether. The insoluble materials are removed by filtration, and the filtrate is concentrated to give (2S)-1-(2-bromoisonicotinoyloxy)- 2-(2-bromoisonicotinoylamino)-3-(3,4-dimethoxyphenyl) propane (5 g).

(3) To a suspension of (2S)-1-(2-bromoisonicotinoyloxy)-2-(2-bromoisonicotinoylamino)-3-(3,4-dimethoxyphenyl) propane (4.68 g) in methanol (100 ml) is added a 1 M lithium hydroxide (8.1 ml), and the mixture is stirred for 15 hours. The reaction mixture is concentrated under reduced pressure to remove the methanol, and the residue is extracted with methylene chloride. The extract is washed, dried, and concentrated. The residue is purified by silica gel chromatography (solvent; chloroform:acetone=5:1) to give (2S)-2-(2-bromoisonicotinoylamino)-3-(3,4-dimethoxyphenyl)-1-propanol (1.2 g).

M.p. 151–153° C.

(4) To a solution of (2S)-2-(2-bromoisonicotinoylamino)-3-(3,4-dimethoxyphenyl)-1-propanol (1.2 g) in dimethylformamide (40 ml) are added potassium carbonate (0.88 g) and copper (I) iodide (0.61 g) at room temperature under nitrogen atmosphere. The mixture is heated with stirring at 120° C. for 30 minutes. To the reaction mixture is added 4-(3-pyridyl)phthalazin-1(2H)-one (1.42 g), and the mixture is heated with stirring at 130° C. for two hours. The reaction mixture is cooled to room temperature, and thereto is added aqueous ammonia. The mixture is extracted with chloroform, and the extract is washed, dried and concentrated. The residue is purified by silica gel chromatography (solvent; chloroform:acetone=1:1) to give (2S)-2-{2-[4-(3-pyridyl)phthalazin-1(2H)-on-2-yl]isonicotinoylamino}-3-(3,4-dimethoxyphenyl)-1-propanol (330 mg).

M.p. 135–137° C.

(5) To a solution of (2S)-2-{2-[4-(3-pyridyl)phthalazin-1(2H)-on-2-yl]-isoniocotinoylamino}- 3-(3,4-dimethoxyphenyl)-1-propanol (200 mg) in methylene chloride (5 ml) are added acetic anhydride (50 μl), triethylamine (80 μl ), and a catalytic amount of dimethylaminopyridine under ice-cooling, and the mixture is stirred at room temperature for two hours. To the reaction mixture are added methanol and a saturated sodium chloride solution under ice-cooling, and the mixture is extracted with chloroform. The extract is washed, dried, and concentrated. The residue is crystallized from ether to give (2S)-2-{2-[4-(3-pyridyl) phthalazin-1(2H)-on-2-yl]isonicotinoylamino}-3-(3,4-dimethoxyphenyl)-1-acetoxypropane (200 mg).

M.p. 118–120° C.

Reference Example 18

(1) To methylene chloride (120 ml) are added 3-(3,4-dimethoxyphenyl)alanine ethyl ester (12.4 g), 2-bromoisonicotinic acid (10.9 g), 1-hydroxybenzotriazole monohydrate (8.23 g) and 1,3-dicyclohexylcarbodiimide (11.1 g), and the mixture is stirred at room temperature overnight. The insoluble materials are removed by filtration, and the filtrate is concentrated. The residue is purified by silica gel chromatography (solvent; chloroform:acetone=10:1) to give N-(2-bromoisonicotinoyl)-3-(3,4-dimethoxyphenyl)alanine ethyl ester (13.9 g) as an oily product.

(2) To a solution of N-(2-bromoisonicotinoyl)-3-(3,4-dimethoxyphenyl)alanine ethyl ester (12.8 g) in tetrahydrofuran (100 ml) is added sodium borohydride (3.3 g), and thereto is added dropwise methanol (15 ml) with heating under reflux over a period of three hours. The reaction mixture is cooled with ice, and thereto is added water. The mixture is extracted with chloroform, and the extract is washed, dried, and concentrated to give 2-(2-bromoisonicotinoylamino)- 3-(3,4-dimethoxyphenyl)-1-propanol (10.2 g).

(3) 2-(2-Bromoisonicotinoylamino)-3-(3,4-dimethoxyphenyl)-1-propanol is treated in the same manner as in Reference Example 17-(4) to give 2-{2-[4-(3-pyridyl) phthalazin-1(2H)-on-2-yl]isonicotinoylamino}-3-(3,4-dimethoxyphenyl)-1-propanol.

M.p. 147–148° C.

(4) 2-{2-[4-(3-Pyridyl)phthalazin-1(2H)-on-2-yl] isonicotinoylamino}-3-(3,4-dimethoxyphenyl)-1-propanol is treated in the same manner as in Reference Example 17-(5) to give 2-{2-[4-(3-pyridyl)phthalazin-1(2H)-on-2-yl]-isonicotinoylamino}-3-(3,4-dimethoxyphenyl)-1-acetoxypropane.

M.p. 85–87° C.

Reference Example 19

(1) 3-(3,4-Dimethoxyphenyl)-L-alanine ethyl ester hydrochloride (66 g), triethylamine (33.3 ml), 2-bromoisonicotinic acid (50.6 g), 1-hydroxybenzotriazole monohydrate (38.4 g) and 1,3-dicyclohexylcarbodiimide (51.7 g) are added to methylene chloride (660 ml), and the mixture is stirred at room temperature for four hours. The reaction mixture is washed, dried, and concentrated. The residue is purified by silica gel chromatography (solvent; chloroform:acetone=10:1) to give N-(2-bromoisonicotinoyl)-3-(3,4-dimethoxyphenyl)-L-alanine ethyl ester (93.5 g).

M.p. 108–109° C.

(2) N-(2-Bromoisonicotinoyl)-3-(3,4-dimethoxyphenyl)-L-alanine ethyl ester is treated in the same manner as in Reference Example 18-(2) to give (2S)-2-(2-bromonicotinoylamino)-3-(3,4-dimethoxyphenyl)-1-propanol.

M.p. 136–138° C.

Reference Examples 20–27

(2S)-2-(2-Bromonicotinoylamino)-3-(3,4-dimethoxyphenyl)-1-propanol and the corresponding heterocyclic compounds of the formula (III-a) are treated in the same manner as in Reference Example 17-(4) to give the compounds as listed in Tables 11 and 12.

TABLE 11

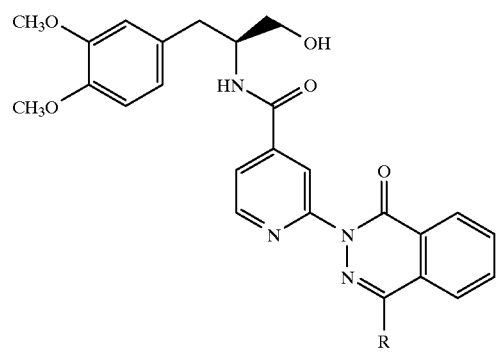

| Ref. Ex. No. | R | Physicochemical properties |
|---|---|---|
| 20 | pyrimidinyl | M.p. 132–135° C. |
| 21 | pyridinyl | M.p. 143–145° C. |
| 22 | 4-(N,N-dimethylamino)phenyl | M.p. 153–155° C. |
| 23 | 3-ethylpyridinyl | M.p. 76–78° C. (powder) |

TABLE 12

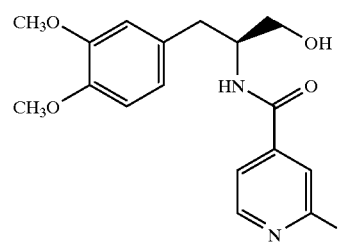

| Ref. Ex. No. | R | Physicochemical properties |
|---|---|---|
| 24 | 5-(2-morpholinoethoxy)-2-methylisoquinolin-1(2H)-one | M.p. 68–70° C. (powder) |
| 25 | 1-methyl-4-(pyridin-4-yl)quinolin-2(1H)-one | M.p. 97–99° C. (powder) |
| 26 | 2-methyl-5-(pyridin-3-ylmethoxy)isoquinolin-1(2H)-one | M.p. 153–156° C. |
| 27 | 1-methyl-4-(pyridin-2-yl)pyridin-2(1H)-one | M.p. 167–170° C. |

Reference Examples 28–35

The pyridine derivatives of the formula (XLVIII) are treated in the same manner as in Reference Example 17-(5) to give the compounds as listed in Tables 13 and 14.

TABLE 13

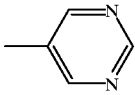

| Ref. Ex. No. | R | Physicochemical properties |
|---|---|---|
| 28 | 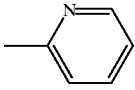 | M.p. 106–109° C. (powder) |
| 29 | 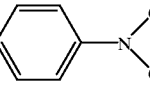 | M.p. 151–153° C. |
| 30 | 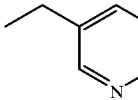 | M.p. 177–178° C. |
| 31 | 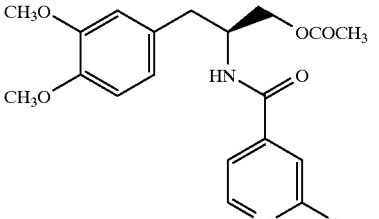 | M.p. 65–67° C. (powder) |

TABLE 14

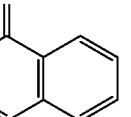

| Ref. Ex. No. | R | Physicochemical properties |
|---|---|---|
| 32 | 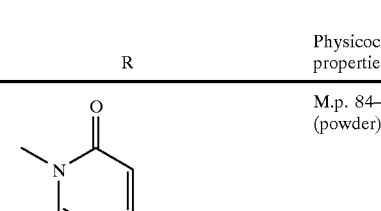 | M.p. 52–55° C. (powder) |

TABLE 14-continued

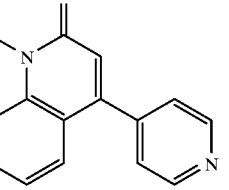

| Ref. Ex. No. | R | Physicochemical properties |
|---|---|---|
| 33 | 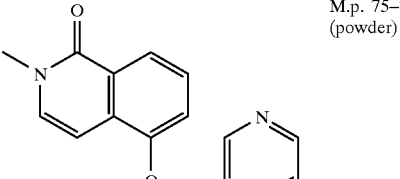 | M.p. 84–87° C. (powder) |
| 34 | 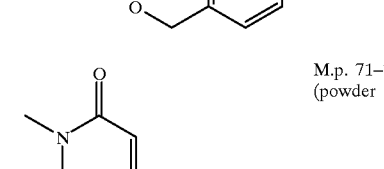 | M.p. 75–77° C. (powder) |
| 35 | 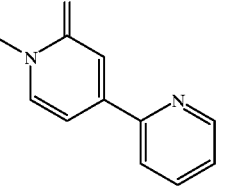 | M.p. 71–74° C. (powder |

Reference Example 36

(1) To acetic anhydride (193 ml) are added 3,4-diethoxybenzaldehyde (234.4 g), N-acetylglycine (95.4 g) and sodium acetate (49.5 g), and the mixture is heated under reflux for one hour, and the reaction mixture is allowed to stand for cooling. The reaction mixture is further allowed to stand in a refrigerator overnight, and then thereto is added water. The mixture is extracted with chloroform, and the extract is washed, dried and concentrated. The residue is crystallized from ethanol to give 4-(3,4-diethoxybenzylidene)-2-methyloxazol-5(4H)-one (100.9 g). M.p. 117–119° C.

(2) 4-(3,4-Diethoxybenzylidene)-2-methyloxazol-5(4H)-one (100 g) is added to acetone (200 ml) and water (400 ml), and the mixture is heated under reflux for 3.5 hours. The mixture is evaporated to remove the acetone, and cooled to room temperature. The precipitates are collected by filtration, and washed with water to give N-acetyl-3-(3,4-diethoxyphenyl)dehydroalanine (99 g). M.p. 190–193° C.

(3) To a suspension of N-acetyl-3-(3,4-diethoxyphenyl) dehydroalanine (100.2 g) in acetic acid (1000 ml) is added 10% palladium-carbon (4 g), and the mixture is subjected to hydrogenation at 40° C. under 3 atms of hydrogen gas for 7 hours. The catalyst is removed by filtration, and the filtrate is concentrated. The residue is crystallized from ether to give N-acetyl-3-(3,4-diethoxyphenyl)alanine (70.1 g).

M.p. 149–151° C.

(4) To 1 M hydrochloric acid (600 ml) is added N-acetyl-3-( 3,4-diethoxyphenyl)alanine (70 g), and the mixture is heated under reflux overnight. The reaction mixture is concentrated to dryness, and the residue is suspended in ethanol (900 ml), and thereto is added drowpise acetyl chloride (200 ml) at −10° C. After addition, the mixture is gradually warmed to room temperature, and the mixture is stirred at room temperature overnight. The reaction mixture is concentrated, and to the residue is added an aqueous potassium carbonate solution, and the mixture is extracted with ethyl acetate. The extract is washed, dried, and thereto is added a 4 M hydrogen chloride in ethyl acetate (60 ml), and the mixture is concentrated. The residue is crystallized from ether to give 3-(3,4-dimethoxyphenyl)alanine ethyl ester hydrochloride (63.4 g).

M.p. 151–152° C.

(5) 3-(3,4-Diethoxyphenyl)alanine ethyl ester hydrochloride is treated in the same manner as in Reference Example 19-(1) and -(2) to give 2-(2-bromoisonicotinoylamino)-3-(3,4-diethoxyphenyl)-1-propanol.

M.p. 97–99° C.

Reference Examples 37–40

2-(2-Bromoisonicotinoylamino)-3-(3,4-diethoxyphenyl)-1-propanol and the corresponding heterocyclic compound of the formula (III-a) are treated in the same manner as in Reference Example 17-(4) to give the compounds as listed in Table 15.

TABLE 15

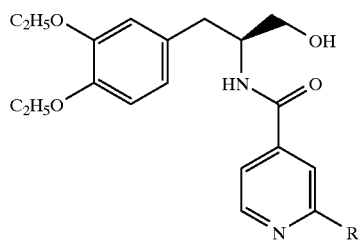

| Ref. Ex. No. | R | Physicochemical properties |
|---|---|---|
| 37 | (N-methyl-phthalazinone-pyridyl) | M.p. 154–155° C. |
| 38 | (1,3-dimethyl-quinazolinedione) | M.p. 163–165° C. |

TABLE 15-continued

| Ref. Ex. No. | R | Physicochemical properties |
|---|---|---|
| 39 | (3-methyl-quinazolinone) | M.p. 150–152° C. |
| 40 | (1-methyl-naphthyridinone) | M.p. 68–70° C. (powder) |

Reference Examples 41–44

The pyridine derivative of the formula (XLVIII) is treated in the same manner as in Reference Example 17-(5) to give the compounds as listed in Table 16.

TABLE 16

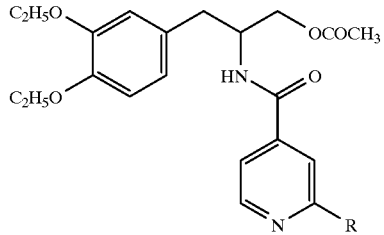

| Ref. Ex. No. | R | Physicochemical properties |
|---|---|---|
| 41 | (N-methyl-phthalazinone-pyridyl) | M.p. 160–163° C. |

TABLE 16-continued

[Structure: C2H5O and C2H5O substituents on benzene ring, connected via CH2-CH(NHC(=O)-pyridyl-R)-CH2-OCOCH3]

| Ref. Ex. No. | R | Physicochemical properties |
|---|---|---|
| 42 | [structure: N-methyl, N'-methyl quinazoline-2,4-dione] | M.p. 47–49° C. (powder) |
| 43 | [structure: 3-methyl-quinazolin-4(3H)-one] | M.p. 55–57° C. (powder) |
| 44 | [structure: 1-methyl-1,6-naphthyridin-2(1H)-one] | M.p. 71–74° C. (powder) |

Reference Example 45

(1) 2-Bromo-4,5-dimethoxybenzaldehyde dimethyl acetal and 2-chloro-N,N-diethylisonitocineamide are treated in the same manner as in Reference Examples 1, 2 and 3 to give 3,4-dimethoxy-6-(2-chloroisonicotinoyl)benzoic acid.

M.p. 201–203° C.

(2) To a solution of 3,4-dimethoxy-6-(2-chloroisonicotinoyl)benzoic acid (70 g) in tetrahydrofuran (1800 ml) is added triethylamine (45.5 ml) at room temperature under nitrogen atmosphere, and thereto is added dropwise ethyl chloroformate (25 ml) at a temperature below −20° C., and the mixture is stirred at −20° C. for 10 minutes. To the reaction mixture is added a 1.38 M aqueous sodium azide solution (500 ml), and the mixture is stirred at room temperature for 1.5 hour, and extracted with ethyl acetate. The extract is washed, dried, and concentrated. The residue is dissolved in toluene (1300 ml), and the mixture is heated under reflux for one hour. To the reaction mixture is added conc. hydrochloric acid (450 ml) under ice-cooling, and the mixture is heated with stirring at 80° C. for one hour. To the reaction mixture is added ice-water, and the mixture is extracted with chloroform. The extract s washed, dried and concentrated. The residue is crystallized from ether to give 3,4-dimethoxy-6-(2-chloroisonicotinoyl)aniline (50.3 g).

M.p. 132–134° C.

Reference Example 46

To 1,2-dichloroethane (150 ml) is added boron chloride (25 g) under ice-cooling, and the mixture is stirred for 15 minutes. To the reaction mixture is added dropwise a solution of 3,4-dimethoxyaniline (36.3 g) in 1,2-dichloroethane (150 ml), and thereto is added 4-cyanopyridine (27.1 g). The reaction mixture is heated under reflux overnight, and thereto is added 2 M hydrochloric acid (160 ml). The mixture is heated with stirring at 80° C. for two hours, and thereto is added a 2 M aqueous sodium hydroxide solution (450 ml) under ice-cooling. The mixture is separated to collect the 1,2-dichloroethane layer, and the aqueous layer is extracted with ethyl acetate. The organic layers are combined, washed, dried and concentrated. The residue is crystallized from ether to give 3,4-dimethoxy-6-isonicotinoylaniline (13.1 g).

M.p. 155–158° C.

Reference Example 47

3,4-Dimethoxyaniline and 4-cyanopyridine-N-oxide are treated in the same manner as in Reference Example 46 to give 3,4-dimethoxy-6-isonicotinoylaniline.N-oxide.

M.p. 192–194° C.

Reference Example 48

To a suspension of 3,4-dimethoxy-6-isonicotinoylaniline (13.1 g) in toluene (100 ml) are added tetronic acid (5.6 g) and p-toluenesulfonic acid monohydrate (9.66 g). The reaction mixture is heated under reflux for 10 hours while the generated water is removed by a Dean-Stark apparatus. The insoluble material are collected by filtration, and thereto is added water. The pH value of the mixture is adjusted to pH 9 with an aqueous potassium carbonate solution, and the precipitated crude crystals are collected by filtration. The resulting crude crystals are recrystallized from dioxane to give 2-hydroxymethyl-4-(4-pyridyl)-6,7-dimethoxy-3-quinolinecarboxylic lactone (14.1 g).

M.p. >220° C.

Reference Example 49

3,4-Dimethoxy-6-isonicotinoylaniline.N-oxide is treated in the manner as in Reference Example 48 to give 2-hydroxymethyl-4-(4-pyridyl)-6,7-dimethoxy-3-quinolinecarboxylic lactone.N-oxide.

M.p. >220° C.

Reference Example 50

To xylene (3 ml) are added 2-hydroxymethyl-4-(4-pyridyl)-6,7-dimethoxy-3-quinolinecarboxylic lactone.N-oxide (677 mg) and 2-chloroquinoline (1.3 g), and the mixture is heated under reflux for 16 hours. The reaction mixture is cooled to room temperature, and thereto is added water. The mixture is extracted with methylene chloride, and the extract is washed, dried, and concentrated. The residue is purified by silica gel chromatography (solvent; chloroform:acetone=2:1) to give 2-hydroxymethyl-4-{4-[2-(quinolin-2(1H)-on-1-yl)]pyridyl}-6,7-dimethoxy-3-quinolinecarboxylic lactone (340 mg).

M.p. >220° C.

Reference Example 51

To a mixture of toluene (20 ml) and trifluoroacetic acid (15 ml) are added 3,4-dimethoxy-6-(2-chloroisonicotinoyl)aniline (10 g) and tetronic acid (3.76 g), and the mixture is heated under reflux for two hours with using a Dean-stark apparatus. The reaction mixture is cooled to room temperature, and the pH value thereof is adjusted to pH 9 with an aqueous potassium carbonate solution, and the mixture is extracted with methylene chloride. The extract is washed, dried, and concentrated. The residue is recrystallized from methanol to give 2-hydroxymethyl-4-[4-(2-chloropyridyl)]-6,7-dimethoxy-3-quinolinecarboxylic lactone (8.26 g).

M.p. 245–246° C.

Reference Example 52

2-Hydroxymethyl-4-[4-(2-chloropyridyl)]-6,7-dimethoxy-3-quinolinecarboxylic lactone is treated in the same manner as in Reference Example 48 to give 2-chloro-4-[2,3-bis(hydroxymethyl)-6,7-dimethoxyquinolin-4-yl]pyridine.

M.p. 196–199° C.

Reference Example 53

3,4-Dimethoxy-6-(2-chloroisonicotinoyl)aniline (10 g) and diethyl ethoxymethylenemalonate (8.2 ml) are heated with stirring at 120° C. to 130° C. for two hours. To the reaction mixture is added ether, and the precipitated crystals are collected by filtration. The resulting crystals (15.1 g) and lithium chloride (6.9 g) are added to dimethylformamide (150 ml), and the mixture is heated under reflux for 45 minutes under nitrogen atmosphere. The reaction mixture is cooled to room temperature, and thereto is added water. The mixture is extracted with ethyl acetate, and the extract is washed, dried, and concentrated. The residue is recrystallized from a mixture of methanol-methylene chloride to give 2-chloro-4-(3-ethoxycarbonylquinoline-6,7-dimethoxy-4-yl)pyridine (4.83

M.po. 191–193° C.

Reference Example 54

2-Chloro-4-(3-ethoxycarbonylquinoline-6,7-dimethoxy-4-yl)pyridine is treated in the same manner as in Example 7-(2) to give 2-chloro-4-(3-hydroxymethyl-6,7-dimethoxyquinolin-4-yl)pyridine.

M.p. 183–185° C.

EFFECTS OF INVENTION

The desired compound (I) of the present invention and a pharmaceutically acceptable salt thereof show an excellent bronchoconstriction inhibitory activity and/or anti-inflammatory activity of airway, and are useful in the prophylaxis or treatment of asthma. That is, the desired compounds (I) of the present invention can effectively inhibit the bronchoconstriction induced by various spasmogens such as histamine, or by antigens.

Besides, the desired compounds (I) of the present invention and a pharmaceutically acceptable salt thereof hardly show any side effects on the heart, but selectively show a bronchoconstriction inhibitory activity and low toxicity, and hence, they advantageously show high safety as a medicament. Although theophylline shows serious side effects on the heart such as hypertension, cardioplamus, etc., the desired compounds (I) of the present invention and a pharmaceutically acceptable salt thereof substantially do not show such side effects but only show an excellent antiasthmatic activity.

What is claimed is:

1. A pyridine derivative of the formula (I):

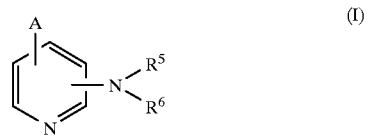

wherein A is a group selected from the following formulae:

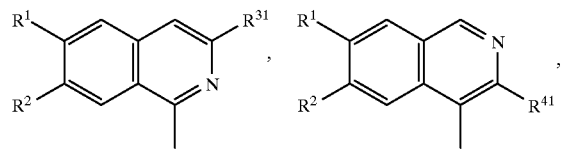

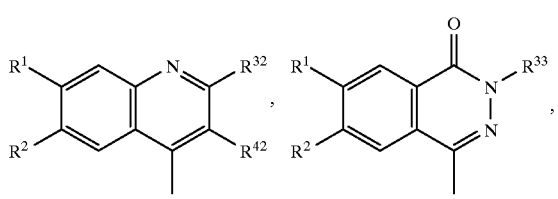

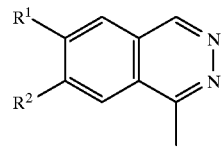

(in which $R^1$ and $R^2$ are the same or different and each a hydrogen atom, or a protected or unprotected hydroxy group, $R^{31}$ is a protected or unprotected hydroxymethyl group, $R^{32}$ is a hydrogen atom, a lower alkyl group, or a protected or unprotected hydroxymethyl group, $R^{33}$ is a substituted or unsubstituted lower alkyl group, $R^{41}$ is a protected or unprotected hydroxymethyl group, $R^{42}$ is a protected or unprotected hydroxymethyl group, and the dotted line means the presence or absence of a double bond), $R^5$ and $R^6$ are the same or different and each a hydrogen atom, or a protected or unprotected amino group, or both may combine at their termini together with the adjacent nitrogen atom to which they bond to form a substituted or unsubstituted heterocyclic group, or a pharmaceutically acceptable salt thereof.

2. The compound according to claim 1, wherein $R^1$ and $R^2$ are the same or different and each a hydrogen atom, a hydroxy group, or a lower alkoxy group, $R^{31}$ is a hydroxymethyl group which may optionally be substituted by a lower alkylcarbonyl group, $R^{32}$ is a hydrogen atom, a lower alkyl group, or a hydroxymethyl group, $R^{33}$ is a lower alkyl group which is substituted by a group selected from a pyridyl group, a cyclo-lower alkyl group, and a hydroxy group, $R^{41}$ is a hydroxymethyl group, and $R^{42}$ is a hydroxymethyl group.

3. The compound according to claim 1, wherein the heterocyclic group formed by combining $R^5$ and $R^6$ at their termini together with the adjacent nitrogen atom to which they bond is a heteromonocyclic, heterobicyclic or heterotricyclic group having optionally, in addition to said adjacent nitrogen atom, a heteroatom selected from a nitrogen atom, an oxygen atom, and a sulfur atom.

4. The compound according to claim 3, wherein the heterocyclic group formed by combining $R^5$ and $R^6$ at their termini together with the adjacent nitrogen atom to which they bond is a pyridyl group, a quinolyl group, an isoquinolyl group, a cyclopenta[b]pyridyl group, a pyrro[2,3-b]pyridyl group, an imidazo[4,5-b]pyridyl group, a pyrido[2,3-d]thiazolyl group, a pyrido[2,3-d]oxazolyl group, a naphthyridinyl group, a quinoxalinyl group, a phthalazinyl group, a quinazolinyl group, an indolyl group, a pyridazinyl group, a thieno[2,3-d]pyridazinyl group, an azepinyl group, an azetidyl group, an isoindolyl group, a pyrrolyl group, a benzazepinyl group, a phenanthridinyl group, a benzothiadnyl group, a benzimidazolinyl group, a pyrazinyl group or a morpholinyl group, these heterocyclic groups optionally being hydrogenated partially or wholly.

5. The compound according to claim 1, wherein the substituents of the heterocyclic group formed by combining $R^5$ and $R^6$ at their termini together with the adjacent nitrogen atom to which they bond are one or two groups which are the same or different and are selected from (1) a lower alkenyl group; (2) a lower alkynyl group; (3) a lower alkylthio group; (4) a cycloalkyl group; (5) a trifluoromethyl group; (6) a cyano group; (7) a tetrazolyl group; (8) a formyl group; (9) an amino group; (10) a mono- or di-lower alkylamino group wherein the lower alkyl moiety may optionally be substituted by a group selected from a morpholino group, a monocycloalkyl-substituted amino group, a pyridyl group, an imidazolyl group, a piperidyl group and a pyrrolidinyl group; (11) a pyridyl group; (12) a morpholino group; (13) a lower alkyl-substituted triazolyl group; (14) a bis(hydroxy-lower alkyl)aminocarbonyl group; (15) a bis(tri-lower alkylsilyloxy-lower alkyl)aminocarbonyl group; (16) a morpholinocarbonyl group; (17) a lower alkyl-substituted piperazinylcarbonyl group; (18) a hydroxy-lower alkyl-substituted piperazinylcarbonyl group; (19) a tri-lower alkylsilyloxy-lower alkyl-substituted piperazinylcarbonyl group; (20) a lower alkoxycarbonyl group; (21) a carboxyl group; (22) a lower alkyl group which may optionally be substituted by a morpholino group or a pyridyl group; (23) a lower alkoxy group which may optionally be substituted by a group selected from a piperidyl group, a pyridyl group, a hydroxy group, and a lower alkoxy group; (24) an oxo group; (25) a hydroxy group; (26) a pyrimidinyl group; (27) a phenyl group which may optionally be substituted by a di-lower alkylamino group or a halogen atom; (28) a halogen atom; (29) a nitro group; (30) an imidazolyl group; (31) a lower alkylenedioxy group; (32) a thiazolyl group; and (33) a thienyl group.

6. The compound according to claim 5, wherein the heterocyclic group formed by combining $R^5$ and $R^6$ at their termini together with the adjacent nitrogen atom to which they bond is a group selected from (1) an oxo-substituted dihydroquinolyl group which may optionally be substituted by a pyridyl group, (2) an oxo-substituted dihydroisoquinolyl group which may optionally be substituted by a group selected from a morpholino-substituted lower alkoxy group and a pyridyl-substituted lower alkoxy group, (3) an oxo-substituted dihydrophthalazinyl group which may optionally be substituted by a group selected from a lower alkyl group being optionally substituted by a pyridyl group; a pyrimidinyl group; a lower alkoxy group; a halogen atom; a pyridyl group; a thiazolyl group; a phenyl group being optionally substituted by a di-lower alkylamino group or a halogen atom; and a thienyl group, (4) an oxo-substituted dihydropyridyl group which may optionally be substituted by a pyridyl group, (5) an oxo-substituted dihydronaphthyridinyl group; (6) a di-oxo-substituted dihydroquinazolinyl group which may optionally be substituted by a lower alkyl group, and (7) an oxo-substituted thienopyridazinyl group which may optionally be substituted by a tri-lower alkoxy-substituted phenyl group.

7. The compound according to claim 1, wherein A is a group selected from the following formulae:

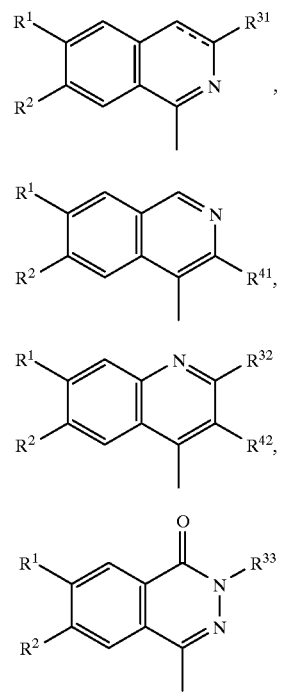

(in which $R^1$ and $R^2$ are the same or different and each a lower alkoxy group, $R^{31}$ is a hydroxymethyl group which may optionally be substituted by a lower alkylcarbonyl group, $R^{32}$ is a hydrogen atom or a hydroxymethyl group, $R^{33}$ is a methyl group which is substituted by a group selected from a cyclo-lower alkyl group and a hydroxy group, $R^{41}$ is a hydroxymethyl group, and $R^{42}$ is a hydroxymethyl group), and the heterocyclic group formed by combining $R^5$ and $R^6$ at their termini together with the adjacent nitrogen atom to which they bond is a group selected from (1) an oxo-substituted dihydroisoquinolyl group which is substituted by a group selected from a morpholino-substituted lower alkoxy group and a pyridyl-substituted lower alkoxy group, (2) an oxo-substituted dihydrophthalazinyl group which may optionally be substituted by a group selected from a lower alkyl group being optionally substituted by a pyridyl group; a pyrimidinyl group; a lower alkoxy group; a halogen atom; a pyridyl group; a thiazolyl group; a phenyl group being optionally substituted by a di-lower alkylamino group or a halogen atom; and a thienyl group, (3) an oxo-substituted dihydronaphthyridinyl group, (4) a di-oxo-substituted dihydroquinazolinyl group, and (5) an oxo-substituted thienopyridazinyl group being substituted by a tri-lower alkoxy-substituted phenyl group.

8. The compound according to claim 1, wherein A is a group selected from the following formulae:

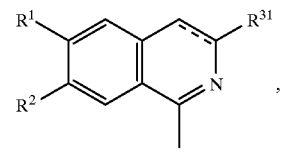

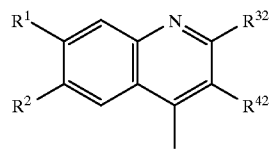

(in which R$^1$ and R$^2$ are the same or different and each a lower alkoxy group, R$^{31}$ is a hydroxymethyl group which may optionally be substituted by a lower alkylcarbonyl group, R$^{32}$ is a hydrogen atom or a hydroxymethyl group, and R$^{42}$ is a hydroxymethyl group), and the heterocyclic group formed by combining R$^5$ and R$^6$ at their termini together with the adjacent nitrogen atom to which they bond is a group selected from (1) an oxo-substituted dihydroisoquinolyl group which is substituted by a group selected from a morpholino-substituted lower alkoxy group and a pyridyl-substituted lower alkoxy group, and (2) an oxo-substituted dihydrophthalazinyl group which may optionally be substituted by a group selected from a lower alkyl group, a pyrimidinyl group, a lower alkoxy group, a pyridyl group, a thiazolyl group, a phenyl group, and a thienyl group.

9. The compound according to claim 1, wherein A is a group of the formula:

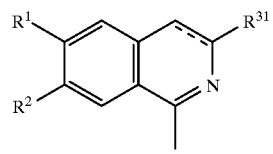

(in which R$^1$ and R$^2$ are the same or different and each a lower alkoxy group, and R$^{31}$ is a hydroxymethyl group which may optionally be substituted by a lower alkylcarbonyl group), and the heterocyclic group formed by combining R$^5$ and R$^6$ at their termini together with the adjacent nitrogen atom to which they bond is a group selected from (1) an oxo-substituted dihydroisoquinolyl group which is substituted by a morpholino-substituted lower alkoxy group, and (2) an oxo-substituted dihydrophthalazinyl group which may optionally be substituted by a group selected from a lower alkyl group, a pyridyl group, and a thiazolyl group.

10. The compound according to claim 1, wherein A is a group of the formula:

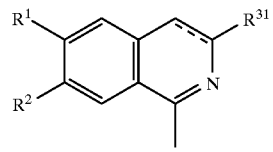

(in which R$^1$ and R$^2$ are the same or different and each a lower alkoxy group, and R$^{31}$ is a hydroxymethyl group which may optionally be substituted by a lower alkylcarbonyl group), and the heterocyclic group formed by combining R$^5$ and R$^6$ at their termini together with the adjacent nitrogen atom to which they bond is a group selected from (1) an oxo-substituted dihydroiso-quinolyl group which is substituted by a group selected from a morpholino-substituted lower alkoxy group and a pyridyl-substituted lower alkoxy group, (2) an oxo-substituted dihydrophthalazinyl group which is substituted by a group selected from a lower alkyl group; a lower alkoxy group; a halogen atom; a pyridyl group; a thiazolyl group; a phenyl group which may optionally be substituted by a di-lower alkylamino group or a halogen atom; and a thienyl group, and (3) an oxo-substituted thienopyridazinyl group which is substituted by a tri-lower alkoxy-substituted phenyl group.

11. The compound according to claim 1, wherein A is a group of the formula:

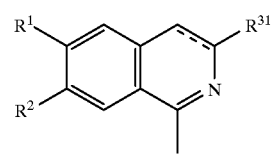

(in which R$^1$ and R$^2$ are the same or different and each a lower alkoxy group, and R$^{31}$ is a hydroxymethyl group), and the heterocyclic group formed by combining R$^5$ and R$^6$ at their termini together with the adjacent nitrogen atom to which they bond is a group selected from (1) an oxo-substituted dihydroisoquinolyl group which is substituted by a group selected from a morpholino-substituted lower alkoxy group and a pyridyl-substituted lower alkoxy group, (2) an oxo-substituted dihydrophthalazinyl group which is substituted by a group selected from a lower alkoxy group; a halogen atom; a pyridyl group; a thiazolyl group; a phenyl group being optionally substituted by di-lower alkylamino group or a halogen atom; and a thienyl group, and (3) an oxo-substituted thienopyridazinyl group which is substituted by a tri-lower alkoxy-substituted phenyl group.

12. The compound according to claim 1, wherein A is a group of the formula:

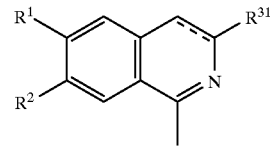

(in which R$^1$ and R$^2$ are the same or different and each a lower alkoxy group, and R$^{31}$ is a hydroxymethyl group), and the heterocyclic group formed by combining R$^5$ and R$^6$ at their termini together with the adjacent nitrogen atom to which they bond is a group selected from (1) an oxo-substituted dihydroisoquinolyl group which is substituted by a morpholino-substituted lower alkoxy group, and (2) an oxo-substituted dihydro-phthalazinyl group which is substituted by a group selected from a pyridyl group and a thiazolyl group.

13. The compound according to claim 1, wherein A is a group of the formula:

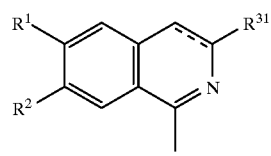

(in which $R^1$ and $R^2$ are the same or different and each a lower alkoxy group, and $R^{31}$ is a hydroxymethyl group), and the heterocyclic group formed by combining $R^5$ and $R^6$ at their termini together with the adjacent nitrogen atom to which they bond is an oxo-substituted dihydrophthalazinyl group which may optionally be substituted by a group selected from a lower alkyl group being optionally substituted by a pyridyl group; a pyrimidinyl group; a lower alkoxy group; a halogen atom; a pyridyl group; a thiazolyl group; a phenyl group being optionally substituted by a di-lower alkylamino group or a halogen atom; and a thienyl group.

14. A pharmaceutical composition which comprises a therapeutically effective amount of a pyridine derivative as set forth in claim 1 in admixture with a conventional pharmaceutically acceptable carrier or diluent.

15. A pharmaceutical composition which comprises a therapeutically effective amount of a pyridine derivative as set forth in claim 7, in admixture with a conventional pharmaceutically acceptable carrier or diluent.

16. A method for prophylaxis or treatment of asthma in a patient, which comprises administering to said patient a therapeutically effective amount of a pyridine derivative as set forth in claim 1.

17. A method for prophylaxis or treatment of asthma in a patient, which comprises administering to said patient a therapeutically effective amount of a pyridine derivative as set forth in claim 7.

\* \* \* \* \*

UNITED STATES PATENT AND TRADEMARK OFFICE
CERTIFICATE OF CORRECTION

PATENT NO. : 5,965,730
DATED : October 12, 1999
INVENTOR(S) : Tatsuzo UKITA et al.

It is certified that error appears in the above-identified patent and that said Letters Patent is hereby corrected as shown below:

On the Title Page, Item [57], in the Abstract, line 4, in the first structure after "formulae:", " 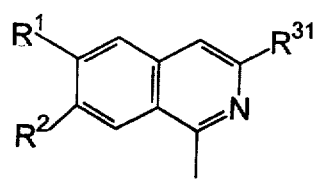 " , should read -- 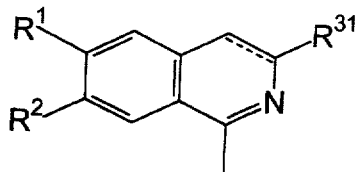 , --.

UNITED STATES PATENT AND TRADEMARK OFFICE
CERTIFICATE OF CORRECTION

PATENT NO. : 5,965,730
DATED : October 12, 1999
INVENTOR(S) : Tatsuzo UKITA et al It is certified that error appears in the above-identified patent and that said Letters Patent is hereby corrected as shown below:

In Claim 1, column 60, in the first structure,

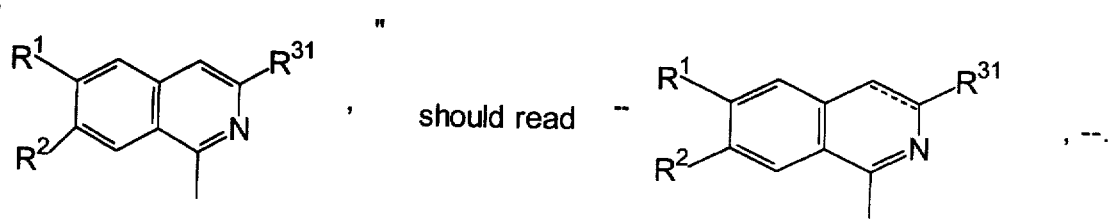

In Claim 4, column 61, lines 4-5, "benzothiadnyl" should read --benzothiadinyl--.

Signed and Sealed this

Twenty-fourth Day of October, 2000

Attest:

Q. TODD DICKINSON

Attesting Officer    Director of Patents and Trademarks